(12) United States Patent
Song et al.

(10) Patent No.: US 10,995,109 B2
(45) Date of Patent: May 4, 2021

(54) INDUSTRIAL PREPARATION METHOD FOR HIGH-PURITY DICYCLOPLATIN NEEDLE-LIKE CRYSTAL

(71) Applicants: Qinhua Song, Jiangsu (CN); Rulin Fan, Jiangsu (CN); Jianke Feng, Jiangsu (CN)

(72) Inventors: Qinhua Song, Jiangsu (CN); Rulin Fan, Jiangsu (CN); Jianke Feng, Jiangsu (CN)

( * ) Notice: Subject to any disclaimer, the term of this patent is extended or adjusted under 35 U.S.C. 154(b) by 0 days.

(21) Appl. No.: 16/473,254

(22) PCT Filed: Jun. 20, 2018

(86) PCT No.: PCT/CN2018/000229
§ 371 (c)(1),
(2) Date: Jun. 25, 2019

(87) PCT Pub. No.: WO2018/233273
PCT Pub. Date: Dec. 27, 2018

(65) Prior Publication Data
US 2020/0140472 A1    May 7, 2020

(30) Foreign Application Priority Data

Jun. 21, 2017 (CN) .......................... 201710472955.0

(51) Int. Cl.
*C07F 15/00* (2006.01)
*A61K 45/06* (2006.01)

(52) U.S. Cl.
CPC .......... *C07F 15/0093* (2013.01); *A61K 45/06* (2013.01); *C07B 2200/13* (2013.01)

(58) Field of Classification Search
CPC .................................................. C07F 15/0093
See application file for complete search history.

(56) References Cited

U.S. PATENT DOCUMENTS

| 6,699,901 B1 * | 3/2004 | Yang ...................... A61P 35/00 |
| | | 514/492 |
| 9,447,130 B1 * | 9/2016 | Liu ...................... C07F 15/0093 |

FOREIGN PATENT DOCUMENTS

| CN | 1311183 | 9/2001 |
| CN | 1314357 | 9/2001 |
| CN | 104122280 | 10/2014 |
| CN | 104127402 | 11/2014 |
| CN | 104693045 | 6/2015 |
| CN | 104693245 | 6/2015 |
| CN | 106132408 | 11/2016 |
| CN | 106995467 | 8/2017 |
| WO | WO-2019161526 A1 * | 8/2019 ........... A61K 31/555 |

OTHER PUBLICATIONS

Peng et al. "One-Pot Method for Preparing Twin Dicarboxylic Acid Diamine Complex Platinum (II) Derivatives." WO-2019161526-A1. English Machine translation of the specification. Downloaded Nov. 7, 2020 from the Internet at <https://patenscape.wipo.int>. (Year: 2020).*

"International Search Report (Form PCT/ISA/210) of PCT/CN2018/000229," dated Aug. 29, 2018, pp. 1-4.

Xuqing Yang et al., "Determination methods for the anticancer drug dicyclopatin, a supramolecule assembled through hydrogen bongding," Analyst, vol. 140, Feb. 2015, pp. 2074-2712.

* cited by examiner

*Primary Examiner* — Amanda L. Aguirre

(57) ABSTRACT

Provided is an industrial preparation method for a high-purity dicycloplatin needle-like crystal, comprising: mixing and reacting carboplatin and 1,1-cyclobutane dicarboxylic acid and water, crystallizing same to obtain a dicycloplatin needle-like crystal with a yield of more than 85%, and a utilization rate of the precious metal platinum of more than 97%. The method is green and environmentally friendly and is suitable for industrial production.

8 Claims, 16 Drawing Sheets

INDUSTRIAL PREPARATION METHOD FOR HIGH-PURITY DICYCLOPLATIN NEEDLE-LIKE CRYSTAL

BACKGROUND OF THE INVENTION

1. Technical Field

The invention relates to a production method of a compound used as medicine. Specifically, it relates to an industrial method of producing the needle-like crystal of Dicycloplatin in high purity.

2. Background Art

Dicycloplatin was classified to the category of I-1 New Medicine according to the Chinese State Food and Drug Administration, which meant that it was an independently invented platinum anti-cancer drug. The inventor of the drug believed that it was generated through the combination of the host molecule carboplatin with a guest molecule 1,1-cyclobutane dicarboxyxlic acid through 4 hydrogen bonds, and had the super-molecular structure as follows:

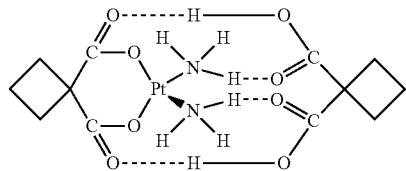

Among the nearly 50 research articles, documents, or patents related to the drug, only 4 patents reported its preparation. The inventor defined the product as a needle-like crystal, which we believe is a reasonable definition because such a crystal provides ample evidence of purity. Considering that Dicycloplatin decomposes into carboplatin and 1,1-cyclobutane-dicarboxylic acid on HPLC column, to determine its purity requires simultaneous calculation of the amount of carboplatin and dicarboxylic acid that have been generated from the decomposition as well as cross-reference check, and this may bring ambiguity to the judgement of product purity. In this context, strict requirements on product traits thus become another level of guarantee for purity. Unfortunately, the preparation procedure disclosed in the inventor's patent could not be repeated. The rest three patents of preparation did not result in the needle crystals required by the inventor, and the purity of their products were fairly poor. We have not found any procedure so far suitable to industrial production.

The inventor's patent CN1311183 A (and CN 1314357 A) described the preparation of Dicycloplatin by 4 examples, namely example 1, 2, 3 and 7. Among them only the example 1 was commenced with carboplatin:

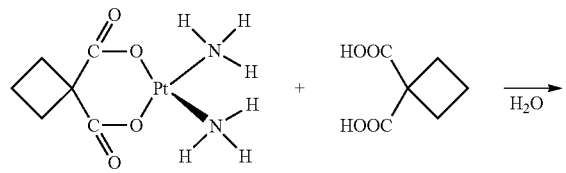

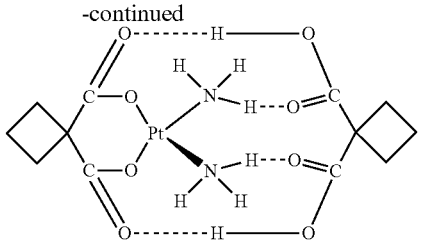

Unfortunately, the example did not mention the purity and melting point of its product. The procedure indicated the amount of both starting materials were 10 mmoles, so the molar ratio of cyclobutane-dicarboxylic acid to carboplatin should be 1 to 1. However, the actual amount used for the preparation in the procedure (carboplatin 3.54 g, cyclobutane-dicarboxylic acid 16.2 g) corresponded to carboplatin (MW 371.3) 9.534 mmoles and dicarboxylic acid (MW 144.1) 112.42 mmoles, suggesting that the molar ratio MRDA/KB became 11.79. We found that neither the ratio of 1 to 1 nor 11.79 to 1 gave sufficiently pure Dicycloplatin crystal by following the procedure of the example, and the product obtained was actually only the starting material carboplatin. Examples 3, 4, 7 in the aforementioned patent were procedures commencing with Cis-platin. They reported melting point of the products in the 182-184° C. range. Among the three examples, the actual amount used for the reaction also did not agree with the numbers of mmoles indicated by the inventor. The inventor did not clarify the necessary reaction parameters. Particularly, all the four examples (including example 1), without exception, treated the crude product through alcohol washing and followed by recrystallization with water. Based on conventional wisdom, chemists would assume that the purpose of alcohol washing was to clean up the impurities generated during the reaction, while water recrystallization was to further purify. However, based on our research, alcohol washing actually caused Dicycloplatin to decompose into carboplatin and dicarboxylic acid, while water decomposed Dicycloplatin even faster and more thoroughly. The needle-like crystal of Dicycloplatin precipitated from aqueous solution, but the crystal could not be in touch of water. The fact seemed to be beyond people's expectation, and could be the reason why chemists failed to obtain sufficiently pure product. In summary, none of the 4 examples of the patent gave the needle-like crystal depicted by the inventor. Alcohol first mostly decomposed the product into dicarboxylic acid and carboplatin. The acid went through the filter into filtrate, water recrystallization of the filter cake further decomposed the remnant of Dicycloplatin completely. The aqueous solution of the recrystallization under cooling could yield only the carboplatin.

The inventor received New Drug Certificate from Chinese FDA in 2012. Two years later, in another of their related patent CN104122280A, they reluctantly admitted the fact of decomposition of Dicycloplatin in water.

The patent CN104693245A also declared a procedure of preparing Dicycloplatin. Example 1 of the document used carboplatin and 1,1-cyclobutane-dicarboxylic acid as starting materials in a molar ratio of 1 to 1. However, the procedure did not mention the appearance of product, and no melting point was reported either. Based on our study, it was absolutely impossible to precipitate needle-like crystal of Dicycloplatin from aqueous solution of carboplatin and 1,1-cyclobutane-dicarboxylic acid in a molar ratio of 1 to 1. The patent procedure did not match the given analysis results. We strictly followed the procedure, and the products obtained were only a mixture in powders.

The patent CN106132408A also declared a procedure of preparing Dicycloplatin. It provided 10 examples. With the exception of example 5 which was in the scale of 118.6 g of carboplatin, all the others performed the preparation in the scale of 15 mg to 5 g. Example 5 spent 417 mmol of dicarboxylic acid and 319 mmol of carboplatin, in a molecular ratio of 1.31. The amount of water used for the preparation was only 5 times to carboplatin in weight. Based on literature reports and our own measurement, the solubility of carboplatin in water was only 1.8%. Even when the dissolution enhancement of dicarboxylic acid was considered, the number was still no higher than 3%. So, in order to form a homogeneous solution at room temperature, the amount of water must be more than 30 times of carboplatin in weight. Since only 5 times of water was used for the preparation, the reaction must be heterogeneous. A heterogeneous reaction at room temperature or even at as low as 5° C. would be difficult to complete and to produce full crystal. Some of the examples did not mention the preparation yield, and none described the product purity. Moreover, the crude products of all the examples were washed with water without any exception, while water could decompose Dicyclopllatin to carboplatin and the dicarboxylic acid quickly and completely. This fact has been admitted by the inventor in their later stage patent CN104122280 A. On page 2 of the document, lines 4 and 7 read: "Dicycloplatin completely decomposed to carboplatin and cyclobutane dicarboxylic acid"; "Dicycloplatin in solutions (aqueous solution for example) decomposed to carboplatin and cyclobutane dicarboxylic acid". So, water washing must affect the purity of the produced Dicycloplatin. The product inevitably contained the carboplatin from decomposition.

Based on our research, in order to obtain sufficiently pure Dicycloplatin crystals, the amount of solvent water must be large enough to make the crystallization process slowly and gently. The Molecular ratio of dicarboxylic acid to carboplatin MRDA/KB must be greater than 3, otherwise the needle-like crystal of Dicycloplatin could not be generated, even if with sufficient amount of water. The inventor pointed out (Determination methods for the anticancer drug dicycloplatin, a supramolecule assembled through hydrogen bonding., Xuqing Yang, Jianwei Zheng, Qinghua Song, et al; Analyst, 2015. 140. 2074-2712.) that evaporating under vacuum or lyophilizing the solution of the mixture of carboplatin and dicarboxylic acid might also generate Dicycloplatin, but the conversion could not be complete, let alone generate nice crystals, therefore it could not become a viable option for industrial application.

Additionally, CN106132408A tried different solvents for the preparation such as alcohol, acetonitrile, isopropynol and so on, resulting in a mixture, the reaction was not complete. It was difficult to separate the remaining carboplatin from the desired product.

Not only did we analyze logically and theoretically the aforementioned three patents related to the production of Dicycloplatin, but we also simulated the procedures of their examples (see also the examples of this application). The results showed that all the existing technologies either could not lead to the correct product, or with purity in significant doubt to satisfy the demand from the Chinese FDA. The scales of their preparations were fairly small, far away from the standard of industrial production. Because of these, we now offer an industrial method of producing highly pure needle-like crystal of Dicycloplatin.

To raise productivity, patent CN 106995467 A described a microwave technique to accelerate the formation of Dicycloplatin in a molecular ratio MRDA/KB of 1 to 1.5. The reaction yield was 65.3% to 90.0%, product purity 81% to 97%, not yet meeting the requirement of the Chinese FDA. The analytical methodology of the product was unclear, and DSC melting point was not reported.

Above patents and articles were cited here as references.

SUMMARY OF THE INVENTION

The purpose of the invention is to provide a procedure of producing highly pure needle-like crystals of Dicycloplatin.

Another purpose of the invention is to provide an industrial method of producing highly pure needle-like crystals of Dicycloplatin.

In order to archive the goal, this invention took the following technical protocol:

The industrial method of producing highly pure needle-like crystals of Dicycloplatin included the following procedures:

(1) Dissolving carboplatin and 1,1-cyclobutane-dicarboxylic acid in water to form a clear solution, running the preparation;

(2) Standing the solution obtained from procedure (1) to crystallize, generating highly pure needle-like crystals of the desired product with no purification.

An industrial method of producing needle-like crystals of dicycloplatin in high purity, characterized in that, including the following procedures: (1) dissolving carboplatin and 1,1-cyclobutane-dicarboxylic acid in water to form a clear solution, allowing them to react; (2) standing the reacting solution of step (1) to crystalize dicycloplatin; wherein crystallization conditions are controlled to obtain a yield of dicycloplatin no higher than 75% to ensure a purity of not lower than 99.5%.

The industrial method of producing needle-like crystals of dicycloplatin in high purity according to claim 1, characterized in that, wherein reaction conditions comprise the following: molar ratio of the 1,1-cyclobutane-dicarboxylic acid to the carboplatin is 4-16, reaction time is 0.5-6 hours, deionized water is used as reaction solvent; room temperature is in a range of room temperature to 50° C.; a ratio of the solvent water to the carboplatin is 30-55 in weight to weight; and wherein the crystallization conditions comprise de-colorization with activated charcoal, cooling the reacting solution to room temperature within 2-8 hours after de-colorization, standing the solution in a dark refrigerator at 10-14° C. for 4-10 days, and then standing in a 0-6° C. refrigerator to crystallize for 15-30 days.

The industrial method of producing needle-like crystals of dicycloplatin in high purity according to claim 1, characterized in that, wherein reaction condition comprise the following: molar ratio of the 1,1-cyclobutane-dicarboxylic acid to the carboplatin is 4-10, reaction time is 0.5-2 hours, the water is deionized water, reaction temperature is in a range of room temperature to 45° C., the room temperature is 10-35° C.; and wherein the crystallization condition comprise de-colorization with activated charcoal, cooling the reacting solution to room temperature within 2-8 hours after de-colorization, standing the solution in a dark ice box at 10-14° C. for 4-10 days, and then standing in a 0-4° C. refrigerator to crystallize for 15-30 days.

The industrial method of producing needle-like crystals of dicycloplatin in high purity according to claim 1, characterized in that, further including step (3), comprising recovering a mother liquor from step (2) and recycling it in 2 to 6 additional cycles, to give an overall yield of dicycloplatin of over 80%; combining the mother liquor with the amount of 1,1-cyclobutane-dicarboxylic acid and of carboplatin consumed by the previous reaction; and repeating step (1) and step (2).

The industrial method of producing needle-like crystals of dicycloplatin in high purity according to claim 1, characterized in that, further including step (4), comprising spraying a product of the dicycloplatin obtained from step (2) or step (3) with pre-cooled isopropanol at 5° C. and pre-cooled ethyl acetate at 5° C. successively.

The industrial method of producing needle-like crystals of dicycloplatin in high purity according to claim 1, characterized in that, further including step (5), comprising concentrating a last mother liquor of step (3) at 55° C. in the dark to recover an additional portion of dicycloplatin product to give a total yield greater than 90%.

The industrial method of producing needle-like crystals of dicycloplatin in high purity according to claim 1, characterized in that, further including step (6), comprising concentrating to dryness a final mother liquor obtained from step (5) at 55° C. in the dark; recovering an amount of 1,1-cyclobutane-dicarboxylic acid by washing with ethyl alcohol or isopropanol, crystallizing a filter cake from water to recover carboplatin, so that a utilization of the carboplatin is over 97%.

The industrial method of producing needle-like crystals of dicycloplatin in high purity according to claim 1 further comprising purifying the dicycloplatin product with an aqueous solution of the 1,1-cyclobutane-dicarboxylic acid or an aqueous solution of both of the 1,1-cyclobutane-dicarboxylic acid and the carboplatin.

The terminology "purification" in the area of chemistry refers to purify product, preferably by recrystallization or column chromatography.

The conditions of the technology are: the molar ratio of 1,1-cyclobutane-dicarboxylic to carboplatin was 4 to 16; reaction time was 0.5 to 6 hours; the water used as solvent was de-ionized water; the reaction temperature was room temperature to 50° C.; Preferably the room temperature was 10 to 35° C. The preferred amount of solvent water was 30 to 55 times of the weight of carboplatin. The preferred condition of crystallization was to allow natural cooling of the reaction solution down to room temperature within 2-8 hours after de-colorization with active charcoal, then stand at 10-14° C. for 4-10 days in dark, finally stand at 0-6° C. in dark for 10 to 15 days.

Preferably, the reaction conditions were: the molar ratio of 1,1-cyclobutane-dicarboxylic to carboplatin was 4 to 10; reaction time was 0.5 to 2 hours; the water used as solvent was de-ionized water; the reaction temperature was room temperature to 45° C.; Preferably the the room temperature was 10 to 35° C.; preferably the amount of solvent water was 40 to 50 times of the weight of carboplatin; preferably the condition of crystallization was that natural cooling the reaction solution down to room temperature within 2-8 hours after de-colorization with active charcoal, then stand at 10-14° C. for 4-10 days in dark, finally stand at 0-4° C. in dark for 15-30 days.

Preferably, the technology included the step (3), namely, recovering the mother liquor from step (2) and applied to next preparation 2 to 6 cycles, so that the overall yield of the product Dicycloplatin was raised to over 85%; preferably, based on the amount of starting materials and the product, or on the results of HPLC analysis, supplementing corresponding amount of 1,1-cyclobutane-dicarboxylic acid and carboplatin into the mother liquor, repeating the procedure (1) and (2).

Preferably, the technology included step (4), namely, let the product Dicycloplatin obtained from step (2) and (3) dry in the air at room temperature, or spraying with pre-cooled to 5° C. isopropanol and ethyl acetate successively.

Preferably, the technology included step (5), namely concentrating the last mother liquor from step (3) below 55° C. in dark to recover an additional part of product Dicycloplatin.

Preferably, the technology included step (6), namely, concentrating thoroughly the final mother liquor from the step (5) below 55° C. in dark until dry, recovering the excessive amount of 1,1-cyclobutane-dicarboxylic acid by washing with ethyl alcohol or isopropanol, crystallizing the filter cake with water to recover carboplatin. The mother liquor from the crystallization was evaporated to dry. The residue was combined with the active charcoal used for de-colorization, and burned up to recover the noble metal platinum so that the utilization of platinum reached to over 97%.

Preferably, the technology included the purification of impure Dicycloplatin with specific solutions; the solutions could be the aqueous solution of 1,1-cyclobutane-dicarboxylic acid, or the aqueous solution of both of 1,1-cyclobutane-dicarboxylic acid and carboplatin.

The invention also provides the application of Dicycloplatin or the mother liquor resulted in the process of Dicycloplatin crystallization to anti-bacteria or anti-virus areas. Preferably, the following bacteria are included: *Staphylococcus aureus, Staphylococcus epidermidis, Bacillus cereus, Bacillus subtilis, Streptococcus* hemolytis-β, *Propionibacterium acnes, Pseudomonas aeruginosa, Klebsiella pneumoniae, Escherichia coli, Helicobacter pylori, Salmonella* typhosa, Plague *bacillus, Vibrio parahemolyticus, Stenotrophomonas maltophilia, Acinetobacter calcoaceticus*, or hepatitis B virus.

The invention produced needle-like crystals of Dicycloplatin, with melting point by DSC measurement of 198-202° C. The melting point number was not only higher than the 182-184° C. reported by the inventor's patent, but also higher than the 198° C. declared by the inventor in their later article (Analyst, 2015. 140. 2074-2712.). XRPD analysis did not show the characteristic peak at 11.4° of carboplatin. HPLC analysis showed both the contents of carboplatin and dicarboxylic acid were in the range of 97-103% and without any impurity peaks. The molar ratio of carboplatin to dicarboxylic acid was in the range of 0.95-1.05 based on analysis, that satisfied the requirements of the inventor. These three HPLC indicators, combined with the shape of crystal, DSC melting point, and the characteristics of XRPD were sufficient to guarantee the product purity to be over 99.9%. The yield of the preparation without the application of mother liquor reached 70%, reaching further to 85% after the application of the mother liquor for several times.

According to the inventor's patent CN1314357A, Dicycloplatin was prepared from 10.0 mmols of carboplatin and 1,1-cyclobutane-dicarboxylic acid, namely, the molar ratio of the two reactants MRDA/KB was 1 to 1. However, our study showed that no Dicycloplatin could be generated at all but only carboplatin. The table 1 listed some of our representative experiments:

TABLE 1

Experiments $MR_{DA/KB}$ equals to 1

| Serial number | KB/mg | DA/mg | $MR_{DA/KB}$ | $H_2O$/KB | Procedure and result |
|---|---|---|---|---|---|
| Expt-I-03-1 -1st | 50.1 | 19.6 | 1.01 | 21.0 | rt, 2.5 hr; 41° C., 3.5 hr; 50° C., 3 hr, cooling down in dark gave particle crystal of carboplatin proved by NMR. |
| Expt-I-03-2-1st | 56.0 | 22.2 | 1.02 | 21.8 | rt, 0.5 hr; 41° C., 3.5 hr; 50° C., 3 hr; rt, 9 hr, cooling down in dark gave white powders of carbopllatin, proved by NMR. |
| Expt-I-05 | 371.6 | 193.1 | 1.34 | 22.61 | 60° C., 17 hr. cooling down in dark gave particle crystal of carboplatin, proved by NMR. |
| Expt-I-09 | 57.6 | 24.1 | 1.08 | 24.2 | 60° C.($t_{bath}$) 5 min fully dissolved, kept the temperature for 45 min, cooling down in dark gave particle crystal of carboplatin; stirred for 25 hrs turned to powder, proved by NMR. |
| Expt-I-03-7 -1st | 62.4 | 24.8 | 1.02 | 26.7 | 50° C., 8 hr; rt, 1 day; cooling down in dark gave very fine crystals of carboplatin. |
| Expt-I-03-3 -1st | 49.1 | 19.6 | 1.03 | 28.1 | rt, 7 hr; 30° C., 5 days, not fully dissolved. |
| Expt-I-03-8 -1st | 46.8 | 18.2 | 1.00 | 33.4 | 50° C., 8 hr; cooling down to rt, 2 pieces of particles precipitated next day, which was carboplatin. |
| Expt-I-03-4-1st | 48.8 | 19.3 | 1.02 | 35.1 | rt, close to clear solution; kept rt for 5 days, cloudy solution, no precipitate. |
| Expt-I-06 | 378.2 | 202.2 | 1.38 | 40.77 | 50° C., 5 hr, not fully dissolved; stirred for 17 hrs; 53° C., 7 hrs; clear solution formed; stand and cooling down gave carboplatin. |
| Expt-I-03-5 -1st | 49.2 | 19.2 | 1.01 | 43.4 | rt, no precipitate by 5 days; then 4° C. for 2 days, gave particles, which was carboplatin. |
| Expt-I-03-9 -1st | 54.1 | 21.0 | 1.000 | 44.9 | 50° C., 8 hr, then rt for 5 days, no precipitate. |
| Expt-III-28 | 5.0 g | 1.90g | 1.00 | 45.0 | 42° C., the product was carboplatin, see also example 1 of this application. |
| Expt-I-03-6 -1st | 52.5 | 20.4 | 1.00 | 61.4 | rt, no precipitate by 5 days; moved into refrigerator for 4 days, no precipitate yet. |
| Expt-I-03-10 -1st | 40.5 | 15.86 | 1.01 | 68.3 | 50° C., dissolved; kept the temp, for 8 hrs; stand at rt for 16 days, no precipitate. |

In summary, when MRDA/KB equaled to 1, no Dicycloplatin could be generated, see also the example 1 of this application.

According to Example 1 of CN1314357A, the amounts of dicarboxylic acid (16.2 g) and carboplatin (3.54 g) were used to the preparation, so the MRDA/KB should be 11.79 to 1 rather than 1 to 1. We found that 'based on this ratio, Dicyclopllatin was indeed generated through "stirring and dissolving." The desired product partly precipitated even at the later stage of the preparation, followed by "rotary evaporated to dry", the residue obtained was a mixture of Dicycloplatin and the excessive 1,1-cyclobutane dicarboxylic acid as crystalline powder.

According to the procedure of the Example, "adding 50 ml of alcohol, stirred for 2 hrs, filtered, washed with alcohol 10 ml×3". Because the solubility of cyclobutane dicarboxylic acid in alcohol was excellent (while Dicycloplatin or carboplatin were only sparingly soluble in alcohol), the excessive dicarboxylic acid entered the filtrate through washing and filtering, Dicycloplatin remained in the filter as cake. That was a white crystalline powder, with yield reaching 95%. The DSC of the crude product showed the existence of carboplatin. Its melting point was higher and with a longer range, reaching 197.7-204.9° C. What was more serious was that, according to the example, the next step was "recrystallization with distilled water." We found that Dicycloplatin decomposed in water to its host molecule carboplatin and its guest molecule dicarboxylic acid thoroughly and completely. So, the crystals obtained from the the "recrystallization with distilled water" were particles proved to be carboplatin by NMR, rather than the tittle compound Dicycloplatin. See also Example 2 of this application.

It it also worth pointing out that "alcohol washing" mentioned in the procedure of CN1314357A was not a safe operation to Dicycloplatin because alcohol may decompose Dicycloplatin. Before the crude Dicycloplatin was washed, the integration of the part of carboplatin peak was 2.00, while dicarboxylic acid peak was 2.05, the ratio of the two was 0.976 to 1 (see also the attached FIG. 1). After washing with ethanol, the integrations became 2.00 and 1.71, the ratio of the two was 1.17 to 1 (see also the attached FIG. 2). The integration weightiness of carboplatin increased, and that was due to the part of carboplatin generated from the decomposition by alcohol, while the dicarboxylic acid resulted from the decomposition entered into filtrate.

1,1-cyclobutane-dicarboxylic acid exhibited solubilization to carboplatin in water. The solubility of carboplatin in water increased with the concentration of 1,1-dicarboxylic acid. When $MR_{DA/KB}$ equaled to 1, carboplatin was easy to precipitate from its aqueous solution; When $MR_{DA/KB}$ equaled to 2, neither Dicycloplatin nor carboplatin precipitated; when $MR_{DA/KB}$ was elevated to 3, a mixture of particle and needle-like crystals precipitated on cooling. The NMR of the two kinds of crystals proved the former as carboplatin while the later as the desired Dicycloplatin. Once $MR_{DA/KB}$ reached 4 to 1, the crystals precipitated from the preparation solution were all needle-like crystal of Dicycloplatin. When the ratio of $MR_{DA/KB}$ was further increased, it was found that the conditions for Dicycloplatin preparation and crystallization were fairly broad. Dicycloplatin needles were easy to be obtained by composing the parameters of reaction temperature, the amount of solvent ($H_2O$/KB), and the crystallization temperature and time.

On the other hand, although the composition of the above parameters in a wide range produced Dicycloplatin needles, different composition may affect not only the precipitation speed, but also the degree of the needle perfection, as well as the peak of its DSC (melting point) and the whiteness of the crystals. The good Dicycloplatin needles should be fine and long, and that was what we obtained.

The preparation solvent was water. Our study discovered that too much water caused the precipitation to be very slow with low yield. On the other hand, when the amount of water was not sufficient, although the yield increased, the appearance of the crystals might not be very good. In order to completely dissolve the starting material, the reaction temperature has to be raised, the product could be contaminated by small amount of by-product impurities and show slightly yellow color. When the precipitation of the needle-like product came out too fast from the solution, the perfection of the crystals could not be guaranteed.

We chose the amount ratio of solvent water to carboplatin as 50 and 45 times, and further studied the influence of $MR_{DA/KB}$ value upon the results of preparation under the ratio. See table 2.

TABLE 2

At $H_2O$/KB = 45(w/w) and 40° C., the results with different ratio of $MR_{DA/KB}$

| Serial number | KB | $MR_{DA/KB}$ | Yield of Dicycloplatin | DSC (mp) °C. | HPLC content, % KB | DA | Molar ratio | Remarks |
|---|---|---|---|---|---|---|---|---|
| Expt-III-16 | 5.0 g | 1.0 | 0% | | | | | Only resulted particles of carboplatin, recovery yield 42.9% |
| Expt-III-17 | 5.0 g | 2.0 | 0% | | | | | No precipitation at 4° C. for 86 days; Divided to two parts; added carboplatin or Dicycloplatin for seeding respectively. Only carboplatin obtained in the two cases. Total recovery 37%. |
| Expt-III-11 | 10.5 g | 3.0 | About 28% | | | | | A mixture of particles and needle-like crystals obtained; as major, the former was carboplatin, yield 28%; the minor was Dicycloplatin, yield 2%. |
| Expt-III-13 | 5.0 g | 4.0 | 47.1% | 197.331 | 100.1 | 99.8 | 1.003 | Dicyclopllatin obtained, as wide and long needles. |
| Expt-III-27 | 5.0 g | 4.0 | 40.3% | 195.589 | 101.9 | 99.9 | 1.020 | Dicyclopllatin obtained, as wide and long needles. |
| Expt-III-19 | 5.0 g | 4.5 | 50.7% | 200.685 | 102.0 | 100.8 | 1.012 | Dicyclopllatin obtained, as wide and long needles. |
| Expt-III-10 | 10.0 g | 5.0 | 57.7% | 199.694 | 100.7 | 100.1 | 0.997 | Dicyclopllatin obtained, as wide and long needles. |
| Expt-III-12 | 20.0 g | 5.0 | 56.6% | 201.223 | 101.4 | 101.6 | 0.998 | Dicyclopllatin obtained, as wide and long needles. |
| Expt-III-20 | 5.0 g | 6.0 | 62.0% | 204.125 | 98.5 | 100.2 | 0.983 | Dicyclopllatin obtained, as wide and long needles. |
| Expt-III-21 | 5.0 g | 7.0 | 69.2% | 199.951 | 101.2 | 100.2 | 1.010 | Dicyclopllatin obtained, as wide and long needles, mixed by fine needles as minor. |
| Expt-III-22 | 5.0 g | 8.0 | 70.6% | 199.285 | 100.5 | 99.96 | 1.005 | Mixture of big and fine needles, the ratio of fine ones increased. |
| Expt-III-23 | 5.0 g | 9.0 | 70.6% | 201.999 | 100.8 | 99.4 | 1.014 | Only fine needles obtained, short. Short. |
| Expt-III-24 | 5.0 g | 10.0 | 73.5% | 199.198 | 98.0 | 97.9 | 1.001 | Fine needles. |
| Expt-III-25 | 5.0 g | 11.0 | 73.5% | 197.289 | 99.9 | 98.9 | 1.010 | Short and wide needles obtained. |
| Expt-III-26 | 5.0 g | 12.0 | 74.9% | 197.006 | 100.6 | 100.1 | 0.995 | Very fine needles. |
| Expt-III-29 | 5.0 g | 14.0 | 73.5% | 195.267 | 101.9 | 101.5 | 1.003 | Needles, fine and concentrated. |
| Expt-III-30 | 5.0 g | 16.0 | 70.6% | 199.193 | 98.6 | 99.7 | 0.989 | Needle-like crystal precipitated immediately at rt after reaction. |

Conclusions: When $MR_{DA/KB}$ was >4 and ≤10, the melting points of the products showed by DSC were over 198° C.; The results of HPLC analysis satisfied the inventor's requirements for quality.

Example 1 of CN 1311183 A did not mention parameters such as reaction temperature and time. We believed that since Dicycloplatin was a super-molecular compound composed by carboplatin and dicarboxylic acid through 4 hydrogen bonds. No anyone of the starting molecules was broken during the product formation. The energy of hydrogen bond was no more than 30 Kcal/Mol usually, much less than the normal covalent bonds. Thus the energy barrier of the formation could not be high and the reaction conditions should be mild. Therefore we set up the preparation temperature in the range of 35 to 45° C.

The reaction solution was de-colorized with active charcoal and filtered. The filtrate was naturally cooled down to room temperature and transferred to 4° C. refrigerator. Crystals were allowed to form, grow with additional precipitations. In order to obtain as much quality products as possible, 15 to 30 days were needed.

Shining colorless needle-like crystals were collected through filtration. They were dried by air at room temperature, or sprayed quickly with isopropanol that was pre-cooled to 5° C. and pre-cooled ethyl acetate successively, and dried under vacuum to finish the final product.

In order to increase the overall yield of the preparation, we supplemented carboplatin, dicarboxylic acid and water to the mother liquid in amounts proportional to the initial reaction cycle after the needle product was separated from the system, and proceed to run the second cycle of the reaction. At first, we supplemented carboplatin and dicarboxylic acid in the amounts equivalent to consumed in the product Dicycloplatin. The second run usually produced the result similar to the first cycle of the preparation. Regarding the supplemented amount of carboplatin, the yield was almost quantitative. However, with additional runs of the cycle and considering unavoidable mechanical loss and side reaction consumptions, we supplemented carboplatin based on the remaining amounts of carboplatin and dicarboxylic acid in the mother liquor that were determined by HPLC. We took advantage of the mother liquor for 4 to 5 cycles, pushing the overall yield to 90%.

The recycle application of the mother liquor increased the utilization rate of the starting materials as shown in table 3.

TABLE 3

The advantage of mother liquid application, calculated on the basis of 1 Kg of carboplatin, $MR_{DA/KB}$ = 6, suppose the yield of each cycle is 60%

| Number of cycles | Mother liquor not applied | | | | Mother liquor applied | | | |
|---|---|---|---|---|---|---|---|---|
| | KB/ g | DA/ g | DCP/ g | yield/ % | KB/ g | DA/ g | DCP/ g | yield/ % |
| 1 | 1000 | 2327 | 833 | 60 | 1000 | 2327 | 833 | 60 |
| 2 | 1000 | 2327 | 833 | 60 | 600 | 233 | 833 | 75 |
| 3 | 1000 | 2327 | 833 | 60 | 600 | 233 | 833 | 81.8 |
| 4 | 1000 | 2327 | 833 | 60 | 600 | 233 | 833 | 85.7 |
| 5 | 1000 | 2327 | 833 | 60 | 600 | 233 | 833 | 88.2 |
| 6 | 1000 | 2327 | 833 | 60 | 600 | 233 | 833 | 90 |
| total | 6000 | 13962 | 4998 | | 4000 | 3492 | 4998 | |

We could see from the table that the overall yield reached 90% by 5 cycles of mother liquor application. For 5 Kg (4998 g) output of Dicycloplatin, 2 Kg of carboplatin and 10.5 Kg of 1,1-cyclobutane-dicarboxylic acid were saved. Namely, 400 g of carboplatin and 2100 g of dicaboxylic acid were saved for each kilogram of the product. The current price of carboplatin was RMB 200,000 per Kg. So, the financial benefit would be significant.

On the other hand, the more application cycles we ran on the mother liquor, the less marginal gain on the overall yield could be obtained from the starting materials. And there was a higher probability to negatively affect the product quality. We thus kept the number of cycles to no more than 5 times.

The product Dicycloplatin produced through our technology was a nice needle-like crystal, identified by NMR, Ms, DSC, X-ray powder diffraction (XRPD), X-ray single crystal diffraction, and proved by anti-tumor activities on various strains of tumor cells. All the results satisfied the requirements from the inventor. The product was proven to be qualified, see also the attached FIGS. 3 to 7. The data of the crystal cells were: a=5.6791(7)Å, b=12.0683(14)Å, c=23.0396(34)Å, α=90.00°, β=95.06(0°), γ=90.00°, V=1572.91(57)Å$^3$, Z=4.

After several recycles, the last remaining mother liquor from the preparation had to be utilized or treated eventually. The technology provided in this application is also a methodology to treat the last remaining mother liquor.

We first moved out 20% to 50% of the mother liquor (depending on how many times the mother liquor was recycled, for the mother liquor that was never cycled, 50% was taken out, see also Example 11 of the application), concentrated under vacuum below 45° C. in dark to dryness. Dissolve the residue in the rest part of the mother liquor at 45° C. Active charcoal 3% was added to de-colorize, stirred for 1 hr at dark, filtered and let the filtrate to crystallize at 12° C. and 4° C. successively. Another crop of needle crystal would then precipitate. The amount was equivalent to 5-10% of the yield. The second mother liquor resulted at the end of this stage.

The second mother liquor was evaporated to dryness under vacuum below 55° C. The residue was a slightly yellow amorphous powder or a crystalline powder. It was treated with isopropanol, stirred at room temperature for 8-12 hrs. The residue in the process was converted to carboplatin and dicarboxylic acid (also contained the impurities generated from the side reactions in the preparation), then filtered. The cyclobutane dicarboxyllic acid entered into the filtrate due to its high solubility in isopropanol. The filtrate provided the recovered dicarboxylic acid after evaporation, which was a pure white powder. The recovery yield was over 90%. It could be used for the next preparation of Dicycloplatin after slightly purification or even no purification. The filter cake was treated with small amount of isopropanol one more time. The majority content of the resulted filter cake was carboplatin. Impurities from the series of preparations and from the concentrations of mother liquor existed in the filter cake as well.

Dicycloplatin kept stable when it co-existed with large excessive amount of dicarboxylic acid in alcohol or isopropanol, while Dicycloplatin alone decomposed in the same solvents. When the crude carboplatin resulted from the decomposition was dissolved in water at 40° C., the Dicycloplatin remnants in the crude decomposed completely. The solution was slightly milky in color, not really clear. It was treated with active charcoal to de-colorize, filtered, and left at 12° C. and 4° C. successively to crystallize. Attention: the crystal obtained in this stage was particles of pure carboplatin.

The mother liquor resulted from the carboplatin purification was evaporated to dry, combined with the waste active charcoal collected from the de-colorization before and burnt to recover the noble metal platinum.

According to the technology, the utilization rate of platinum reached 97%.

tin remained in the mother liquor, which could be treated by the procedure mentioned before.

Lastly, we would like to compare our industrial method with the existed procedures.

TABLE 4

The comparison of our technology with existing techniques

| Patent | Examples | Appearance of product | Melting point | Purity | X-ray single crystal diffraction | Yield % | Washing | Remarks |
|---|---|---|---|---|---|---|---|---|
| CN1311183 A | 1 | Particle (FIG. 11) | | 0% | surely carboplatin | | Alcohol washing | Not desired product |
| CN1311183 A | 2 | Particle | | 0% | Surely carboplatin | | Alcohol washing | Not desired product |
| CN104693045 A | 3 | Amorphous powder | | mixture | No single crystal, NA | 100 | No washing | Not crystal, hard to identify |
| CN106132408 A | 4 | NA | | Not tidy crystals | No single crystal, NA | | Water washing | powders |
| CN106132408 A | 5 | | | mixture | No single crystal, NA | | Water washing | powder of Mixture |
| Present application | 6 to 11 | Needle-like crystal (FIGS. 7A, 7B) | 198-202° C. | Completely qualified | Match structure, see FIGS. 3-5, 6a, 7, 8a | >90 | Isopropanol, then ethyl acetate spraying | Shining colorless needle-like crystals |

The technology was concise and rigorous. The utilization rate of starting materials was very high, it was environmental friendly and is suitable for industrial production.

The Purification of Dicycloplatin

Dicycloplatin decomposes with water, so it could not be recrystallized with water. Dicycloplatin does not dissolve in most of organic solvents, so it could not be purified with organic solvent such as alcohol or acetone. The problem bothered some researchers, and made the product quality unstable. As a complete industrial method, a purification process must be included. Unqualified product could not be absolutely avoided during production whether they were from objective reasons or subjective errors. Therefore, we invented a procedure of recrystallization as follows.

Step one, prepare the recrystallization solution.

Number 1 solution: for each mole of impure of Dicycloplatin, dissolve cyclobutane dicarboxylic acid (11 mole) and carboplatin (1 mole) in water (65 weight times of the impure Dicycloplatin that needs to be purified).

Number 2 solution: for each mole of impure of Dicycloplatin, dissolve cyclobutane dicarboxylic acid (5 moles) in water (32 weight times of the amount of the Dicycloplatin that needs to be purified).

Step two, dissolving 1 mole of impure Dicycloplatin in the aforementioned number 1 solution at 30-50° C., de-colorizing at the same temperature for 1 hour; filter. The filtrate was crystallized through the procedure of Dicycloplatin preparation.

The yield of the purification was 100% to 120%. The reason why the yield could be so high was a part of the carboplatin in Solution 1 was also converted to Dicycloplatin. The mother liquor from the purification could be treated by the procedure mentioned before.

Alternative: dissolving 1 mole of impure Dicyclopllatin in Solution 2 at 30-50° C., de-colorize for 1 hr at the same temperature, filter. The filtrate was crystallized through the procedure of Dicycloplatin preparation. The yield of the recrystallization was around 60%. A part of the Dicycloplatin remained in the mother liquor, which could be treated by the procedure mentioned before.

BRIEF DESCRIPTION OF THE DRAWINGS

FIG. 7b shows the representative picture of Dicycloplatin crystals obtained in the preparation scale over 25 g, the crystal was still needle-like;

DETAILED DESCRIPTION OF THE INVENTION

The following examples further illustrate our invention. It has to be emphasized that all the procedures applied in the examples are merely exemplary in nature, and are in no way intended to limit the invention, application or uses. Various simple improvements under the premise of this invention conception shall be covered within the scope of the protection of this invention. If not specified otherwise, all the starting materials or reagents used in this invention were domestically available.

Analytical Instruments

1, Melting point measurement: micro-melting point measurement instrument, model X-5, Yu-Hua corporation Ltd.;

2, X-ray powder diffraction analysis: XRPD measurement instrument, D8 ADVANCE X-ray diffraction instrument, Bruker corporation Ltd, Germany;

3, Nuclear magnetic resonance measurement instrument, BRUKER AVENCE II, 400 MHz, Bruker corporation Ltd., Switzerland;

4, Differential scanning calorimeter (digital security controls), NETZSCH, model DSC204F1, 2005, Germany;

5, X-ray single crystal diffraction: CCD Single crystal X-ray diffractometer, Japanese Neo confusionism, SATURN 724+.

6, High performance liquid chromatography: Agilent 1260 Infinity II HPLC instrument, Agilent 1260 Infinity II ultra-violet detector, ICC Integrated column temperature box, Agilent 1260 Infinity II automatic sampler, Agilent Open LAB CDS work station Condition of HPLC: column, Poroshell 120 EC-C18 4.6×150 mm, 4 um; mobile phase, PH 3.0 phosphate buffer solution: methanol=95:5; flow rate: 1 ml/min; injection volume: 5 ul; column temperature: 40° C.; wave length: 220 nm.

Figure 8A:
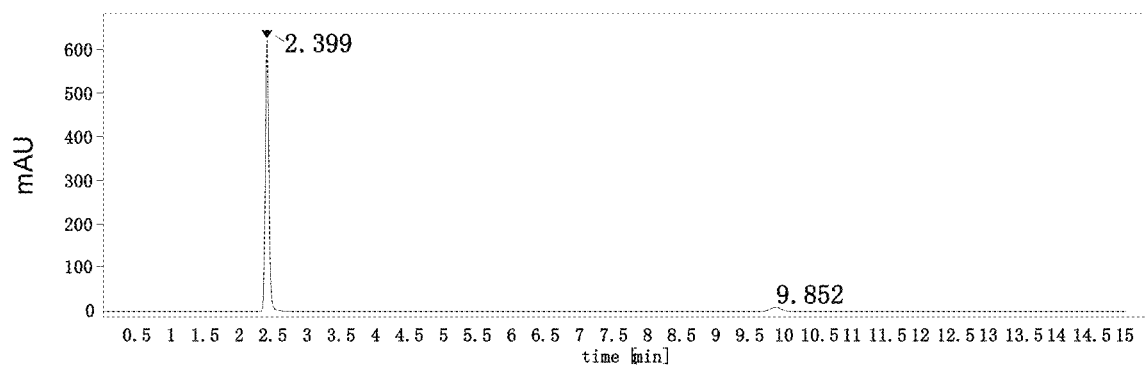
FIG. 8a shows the representative HPLC trace of Dicycloplatin.
Figure 8B:
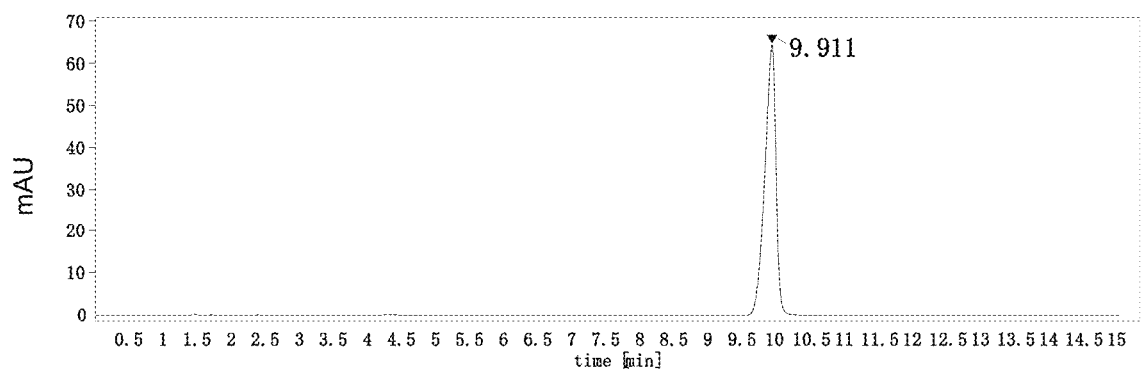
FIG. 8b shows the representative HPLC trace of carboplatin.
Figure 8C:
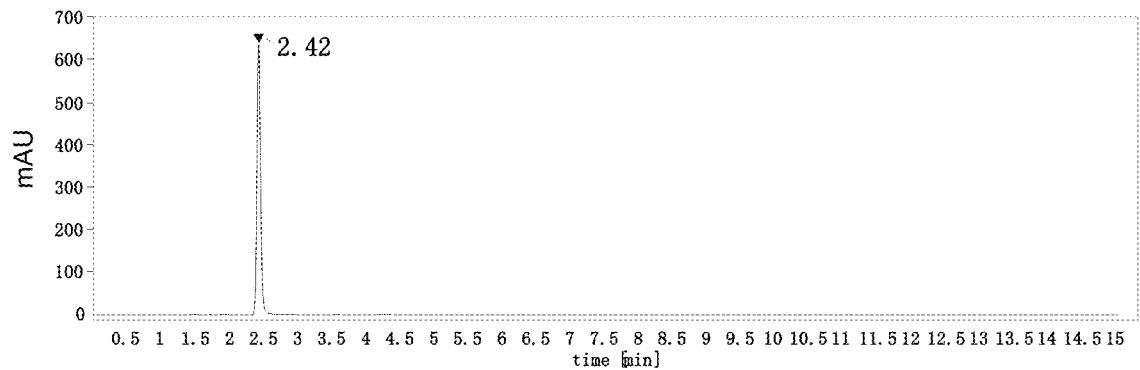
FIG. 8c shows the representative HPLC trace of 1,1-cyclobutane dicarboxylic acid.

FIGS. 8a-8c showed the HPLC traces of Dicycloplatin, carboplatin, and 1,1-cyclobutane-dicarboxylic acid.

Examples 1 and 2 checked the Dicycloplatin inventor's patent CN1311183A (and CN1314357A). Example 3 checked the existing patent CN104693245A. Examples 4 and 5 checked the existing patent CN106132408A.

Example 1: Simulated the Example 1 of the Inventor's Patent CN1311183A, Used the Ratio of 1,1-Cyclobutane Dicarboxylic Acid to Carboplatin $MR_{DA/KB}$ Equaled to 1 to 1 (See Also the Tables 1 and 2 of the Summary of the Invention.)

Figure 9:
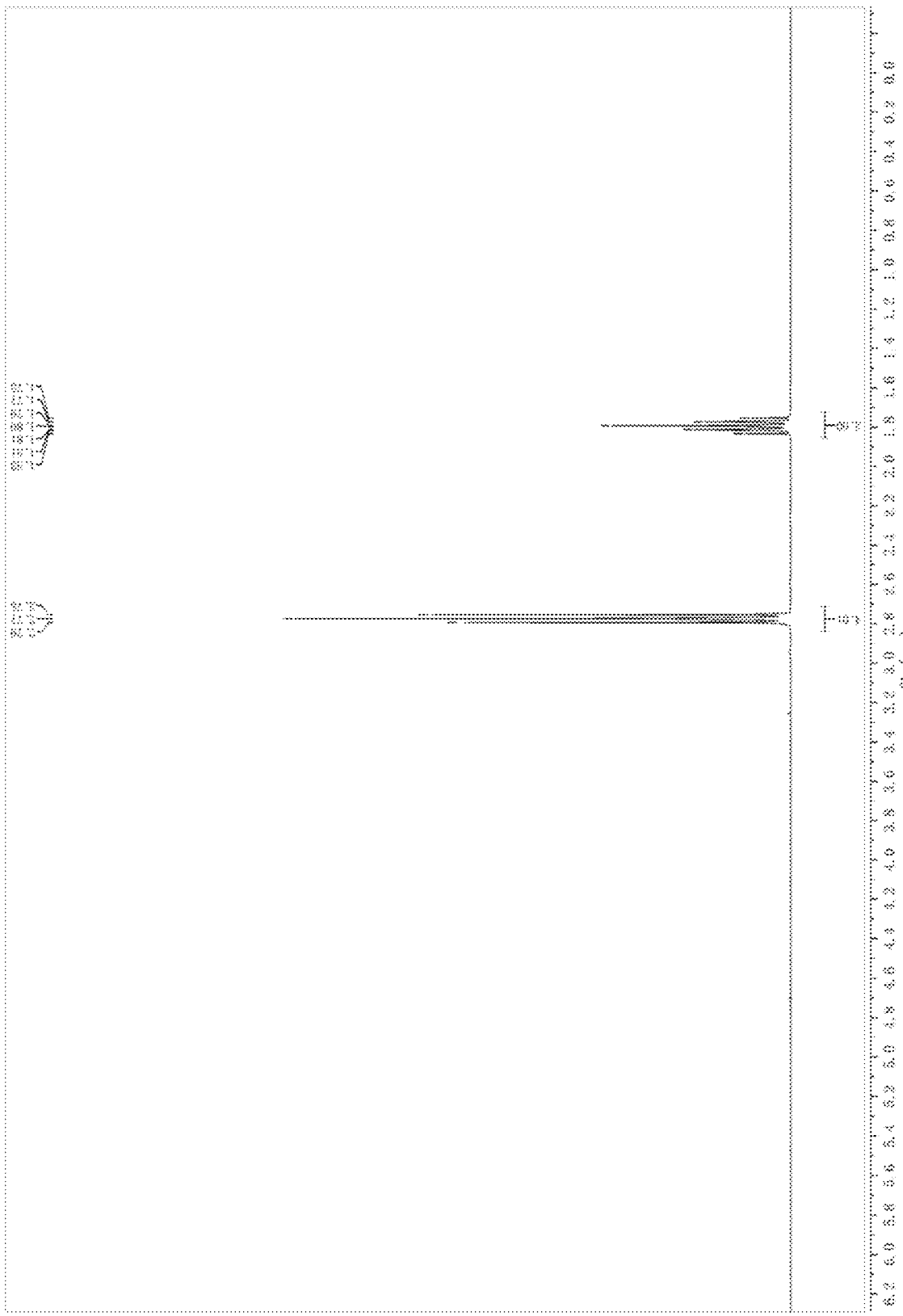
FIG. 9 shows the representative $^1$H-NMR of the crystal product obtained from Example 2, which is carboplatin.

Added carboplatin 3.5464 g (9.5513 mmol) into 200 g pure water (water/KB=56.4), stirred at 42° C. (bath temperature) for about 25 minutes to fully dissolve, under the condition of avoiding direct light. 1,1-cyclobutan dicarboxylic acid 1.3789 g (9.5690 mmol, $MR_{DA/KB}$=1.0) was added into the solution. Stirring was then continued for more than 30 min. The reaction solution was evaporated under vacuum at 55° C. (bath temperature) to dryness. Into the residue 50 ml of absolute alcohol was added, stirred at room temperature for 2 hours; filtered; the filter cake was washed with alcohol 10 ml×3. The filter cake weighed 3.7 g after drying under vacuum. It was added into 130 ml of pure water, stirred to fully dissolve at 42° C. Filtration yielded a clear solution. It was then moved into 12° C. refrigerator to cool. Particle crystals precipitated 5 days later. It was further moved into 4° C. refrigerator for 6 more days. Filtration gave crystal product, weighing 1.21 g, recovery yield 34.1%. Its NMR was the same as the product from Example 2 (see also FIG. 9), shown to be carboplatin. Melting point 227.5° C. (decomp. and tarred), same as the commercial product of carboplatin (mp 227.4° C., decomp. and tarred).

Example 2: Simulated the Example 1 of the Inventor's Patent CN1311183A, Used the Ratio of 1,1-Cyclobutane Dicarboxylic Acid to Carboplatin $MR_{DA/KB}$ Equaled to 11.79

The example followed strictly the procedure of Example 1 of Dicycloplatin inventor's patent CN1311183A, but the reaction was scaled up (the amount of carboplatin was increased up to 5.0 g from 3.54 g and cyclobutane dicarboxylic acid was increased to 22.9 g from 16.2 g correspondingly. The amount of solvent water and alcohol used for washing afterwards were increased proportionally.)

Figure 1:
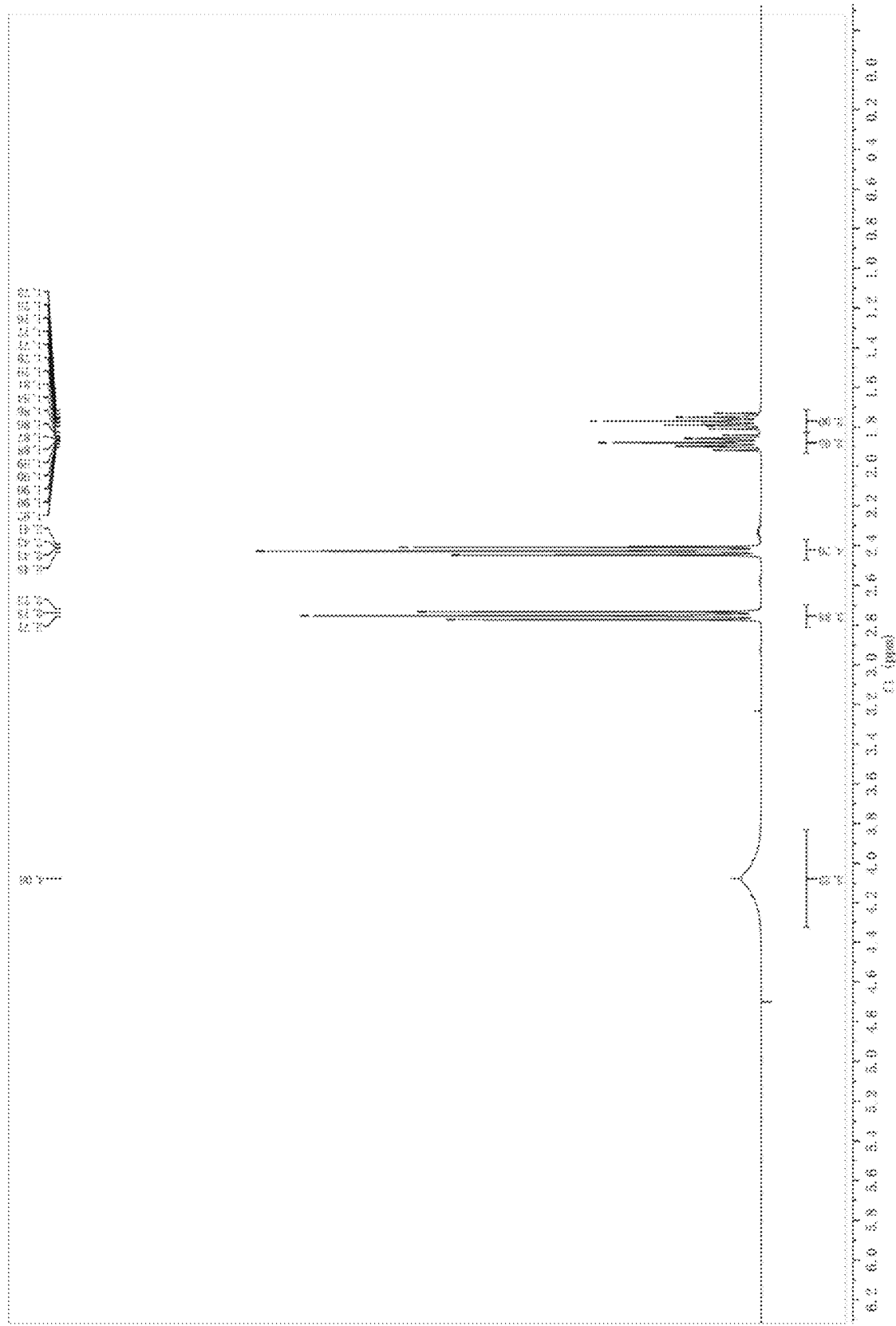
FIG. 1 shows the representative $^1$H-NMR spectrum of the Dicycloplatin precipitated from preparation of Example 2, the integration ratio of the cyclobutane of dicarboxylic acid part to the cyclobutane of carboplatin part was 2.05 to 2.00, which means that the product was Dicycloplatin but adsorbing small amount of dicarboxylic acid.

5.0 g carboplatin (13.47 m mol) was added into 488.6 g of pure water, stirred at room temperature for 35 min to dissolve, then 22.9 g (158.9 m mol) of 1,1-cyclobutane dicarboxylic acid was added (the molar ratio to carboplatin $MR_{DA/KB}$ equaled to 11.79), a fully clear solution was generated 5 min later. The solution turned milky in appearance 10 min later, a fine crystal started to precipitate. A few particles of the crystal were picked out with a specular for NMR measurement, NMR (see also FIG. 1): ($D_2O$) δ, 1.79, pent, 2H (2.00, the part of carboplatin); 1.89, pent, 2H, (2.05, the part of dicarboxylic acid); 2.43, t, 4H (the part of dicarboxylic acid); 2.75, t, 4H (the part of carboplatin). It was estimated based on the integrals of carboplatin part (2.00) and to dicarboxylic acid part (2.05) that the product at this stage was Dicycloplatin mixed by dicarboxylic acid at around 3%.

Figure 2:
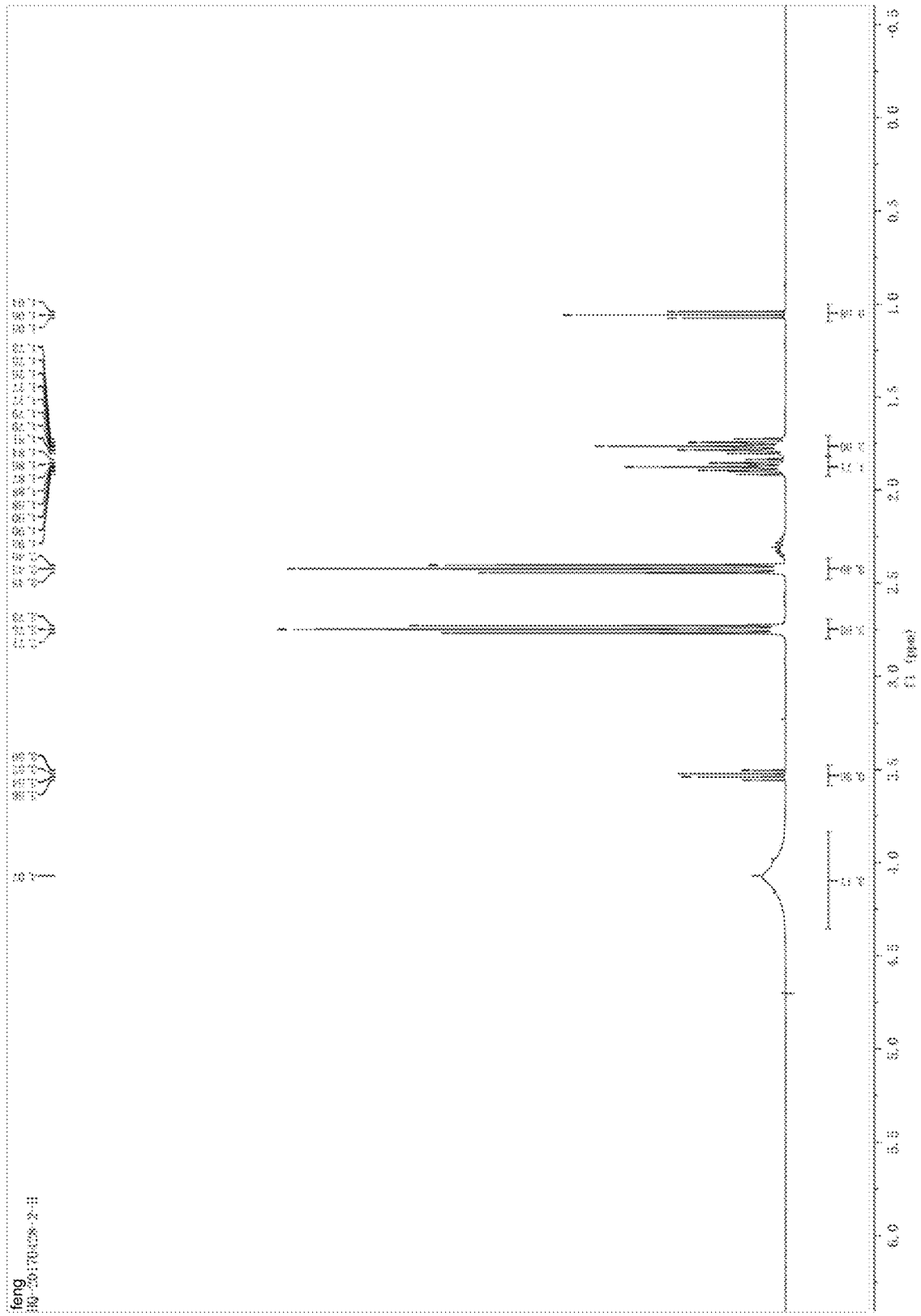
FIG. 2 shows the representative $^1$H-NMR spectrum of the product washed with alcohol. Because alcohol decomposed a part of Dicycloplatin to dicarboxylic acid and carboplatin, the acid was washed out. So, the integration ratio of the cyclobutane of dicarboxylic acid part to the cyclobutane of carboplatin part was 1.71 to 2.00, which means that the product was Dicycloplatin mixed with substantial amount of carboplatin.
Figure 3:
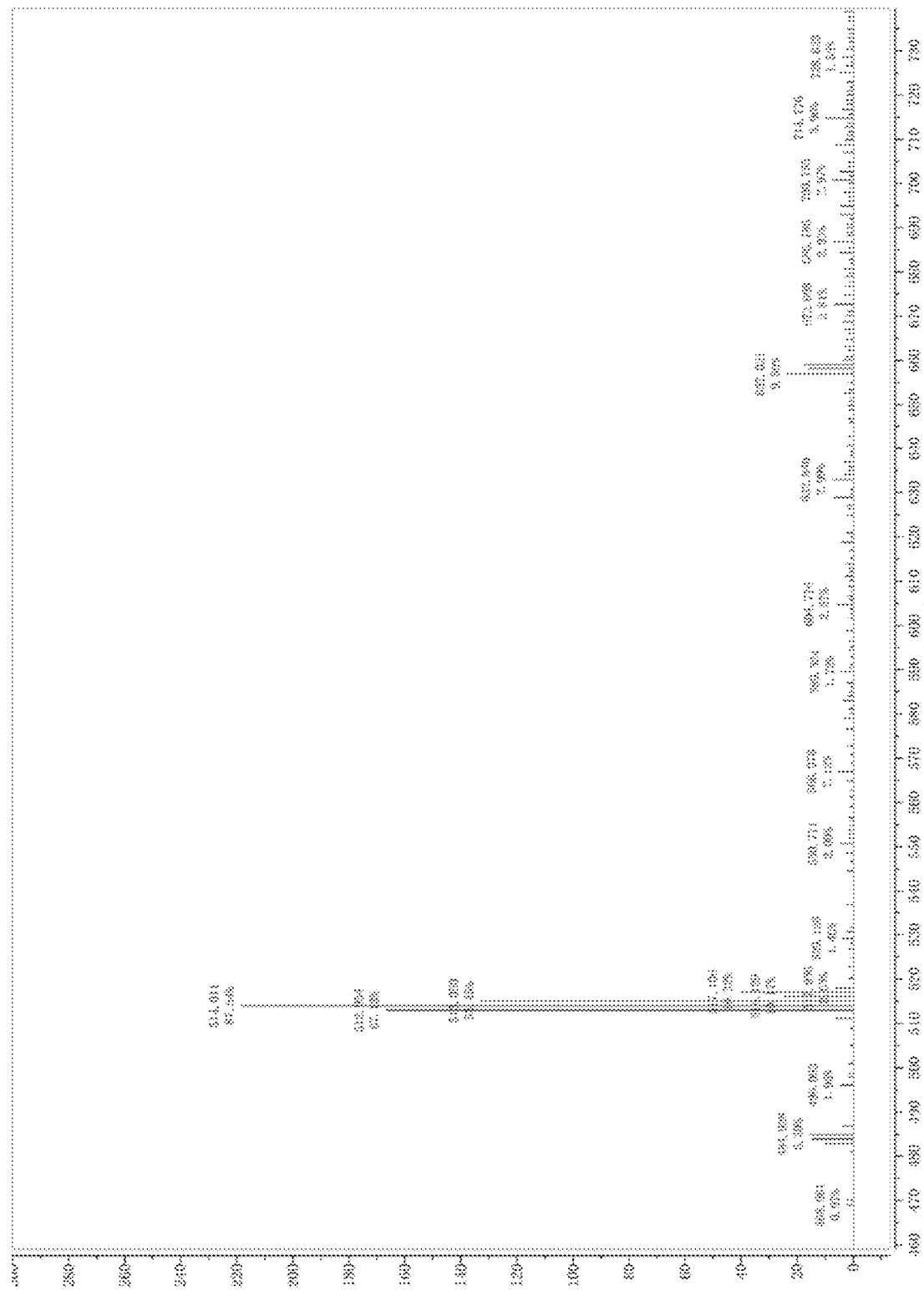
FIG. 3 shows the representative Ms spectrum of the product Dicycloplatin of example 6.
Figure 4:
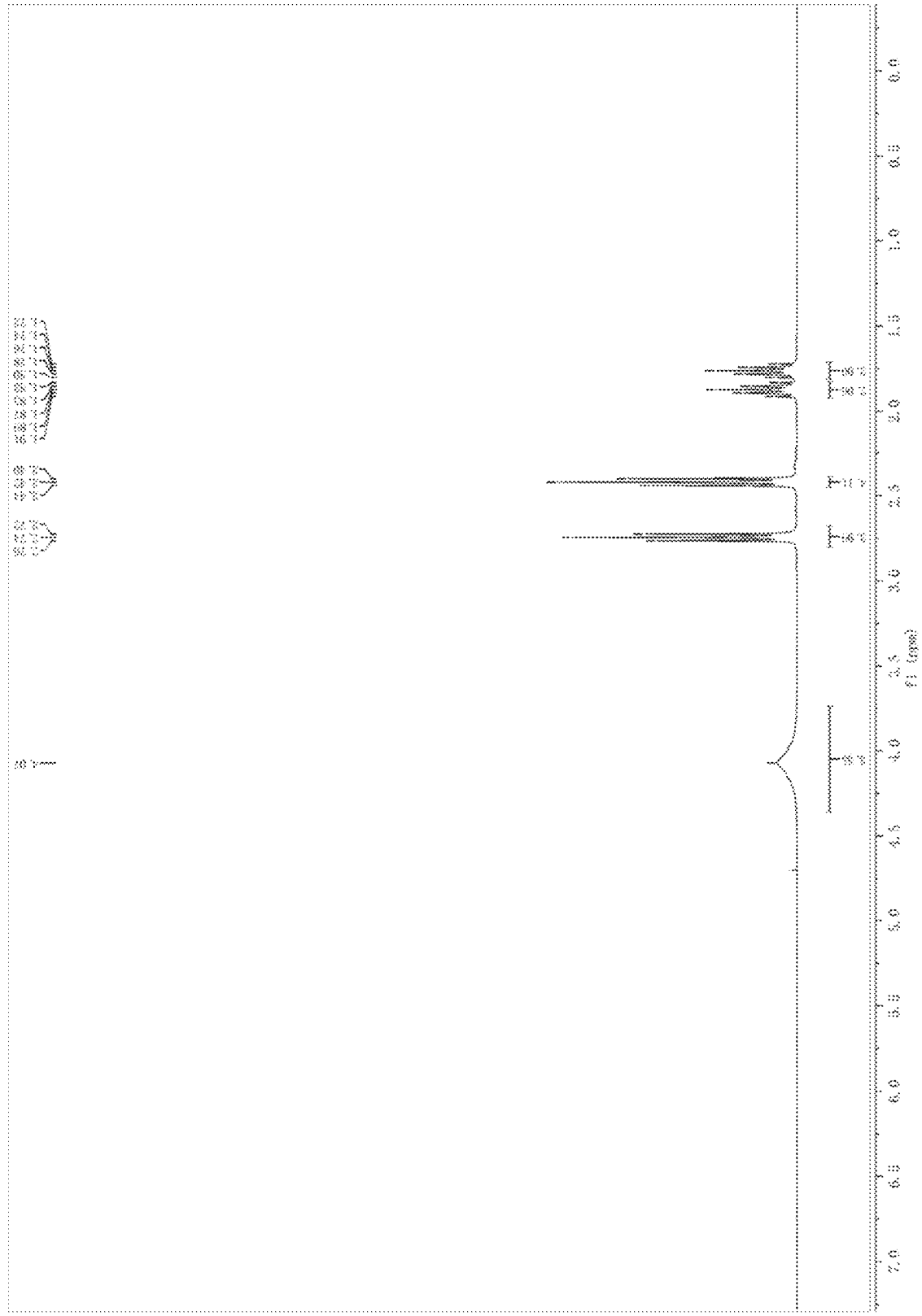
FIG. 4 shows the representative $^1$H-NMR spectrum of the product Dicycloplatin of example 6.
Figure 5:
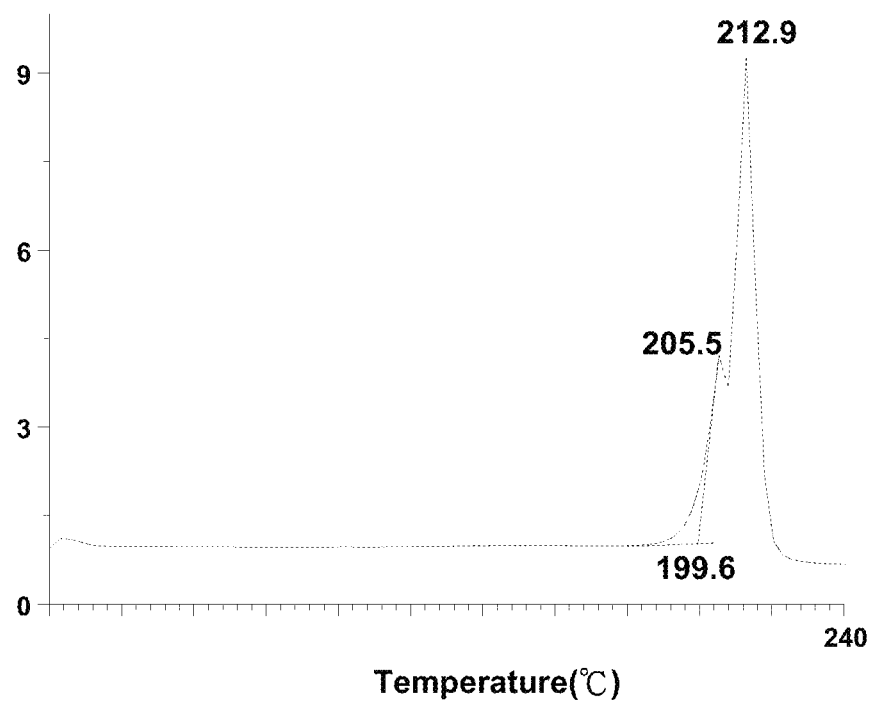
FIG. 5 shows the representative DSC curve of the product Dicycloplatin of example 6, that showed a melting point of 199.6° C.
Figure 6A:
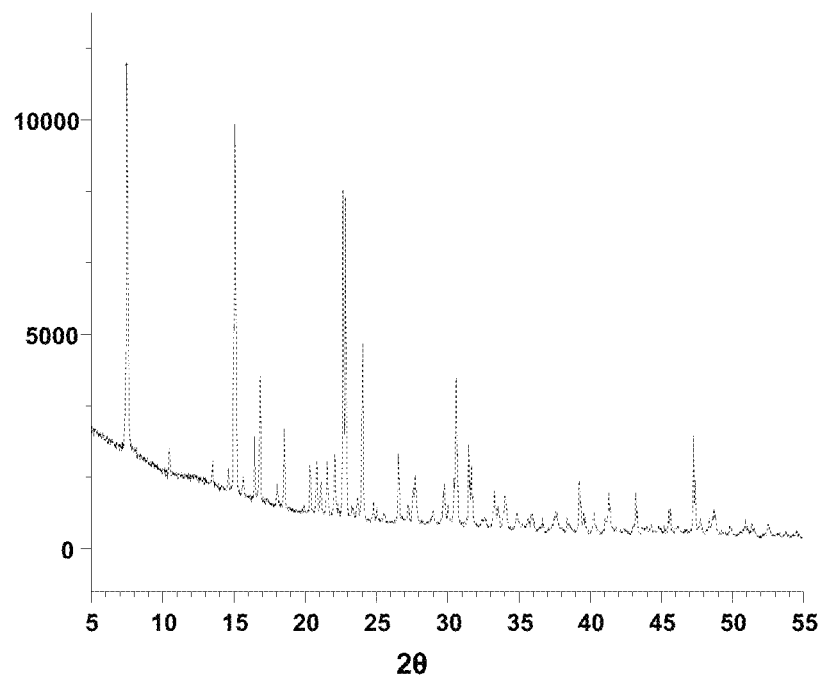
FIG. 6a shows the representative XRPD spectrum of the product Dicycloplatin of Example 6. The diffraction peak at 11.4° corresponding to carboplatin did not appear at all, which means that the product did not contain carboplatin.
Figure 6B:
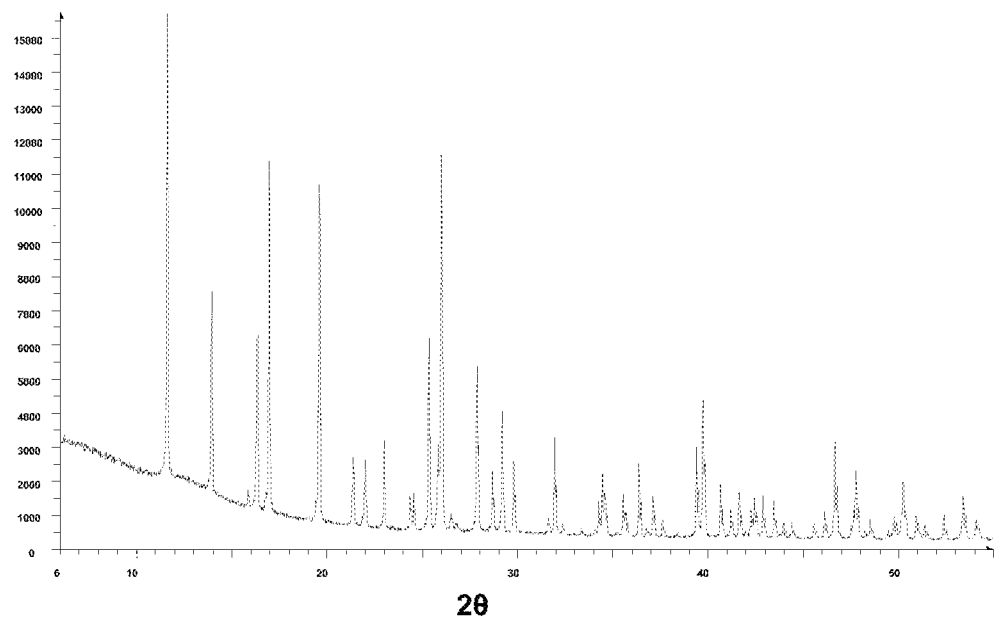
FIG. 6b shows the representative XRPD spectrum of carboplatin, which shows the characteristic peak of diffraction at 11.4°.
Figure 6C:
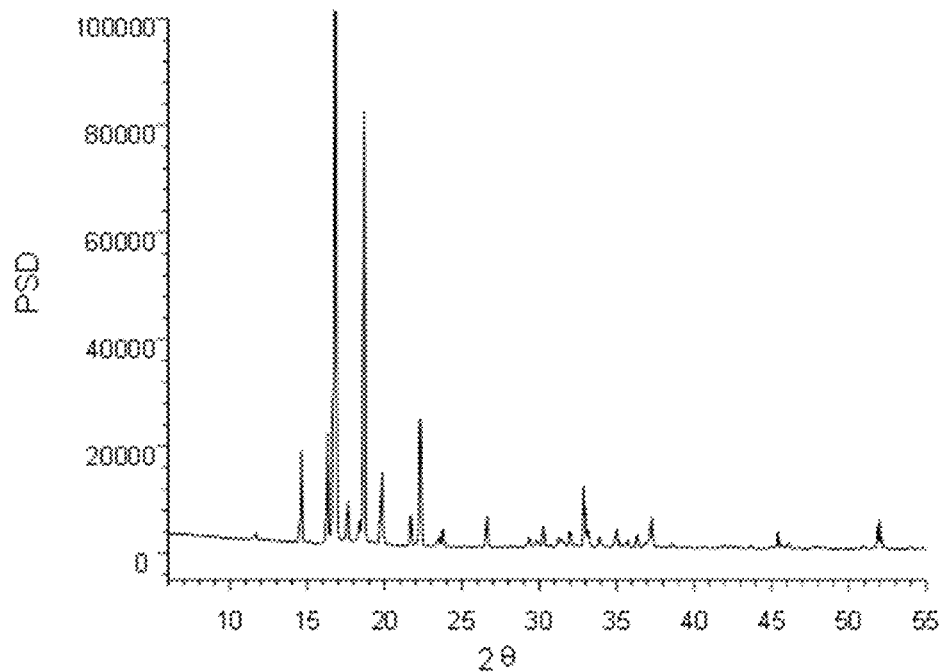
FIG. 6c shows the representative XRPD spectrum of 1,1-cyclobutane dicarboxylic acid.
Figure 7A:
FIG. 7a shows the representative picture of Dicycloplatin needle-like crystals.
Figure 7B:
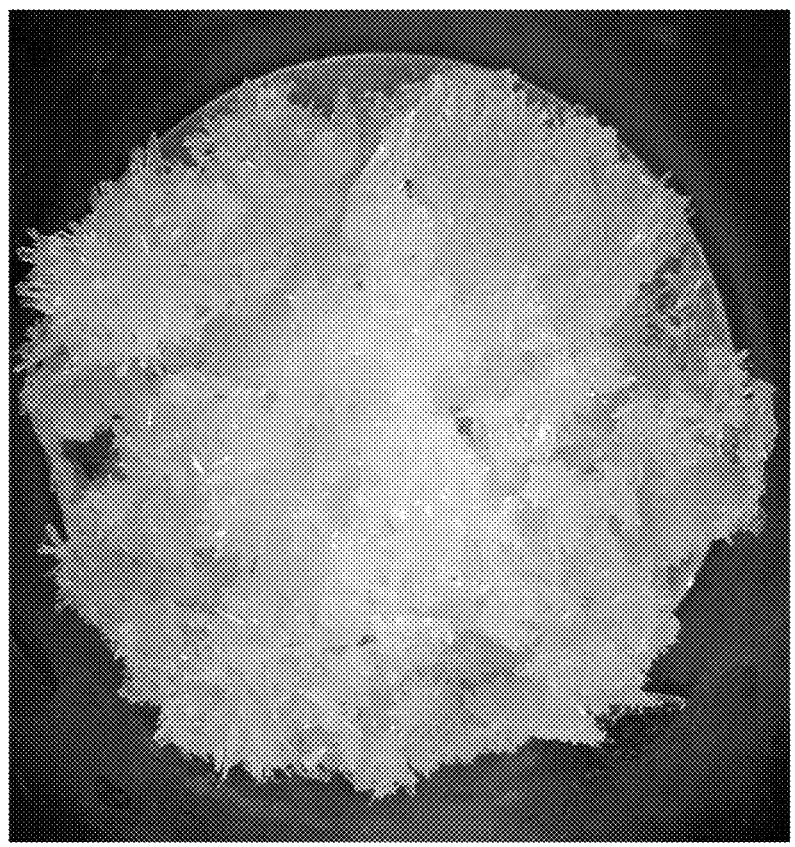

According to the procedure of Example 1 of the inventor's patent, the reaction mixture was stirred for more 25 min, evaporated at 60° C. (bath temperature) to dryness, 27.7 g of powders was obtained. Into the cake 70.6 ml of absolute alcohol was added, stirred for 2 hours at room temperature; filtered; the filter cake was washed with alcohol 14 ml×3, the filter cake weighed 6.6 g after vacuum dried. NMR (see also FIG. 2): ($D_2O$) δ, 1.77, pent, 2H (2.00, the part of carboplatin); 1.88, pent, 2H, (1.71, the part of dicarboxylic acid); 2.43, t, 4H (the part of dicarboxylic acid); 2.75, t, 4H (the part of carboplatin). It was estimated based on the integral corresponding to carboplatin (2.00) and to dicarboxylic acid (1.71) that the product at the stage was Dicycloplatin mixed by carboplatin at around 15%. The melting point of the product was 197.3-204.9° C.

Figure 10:
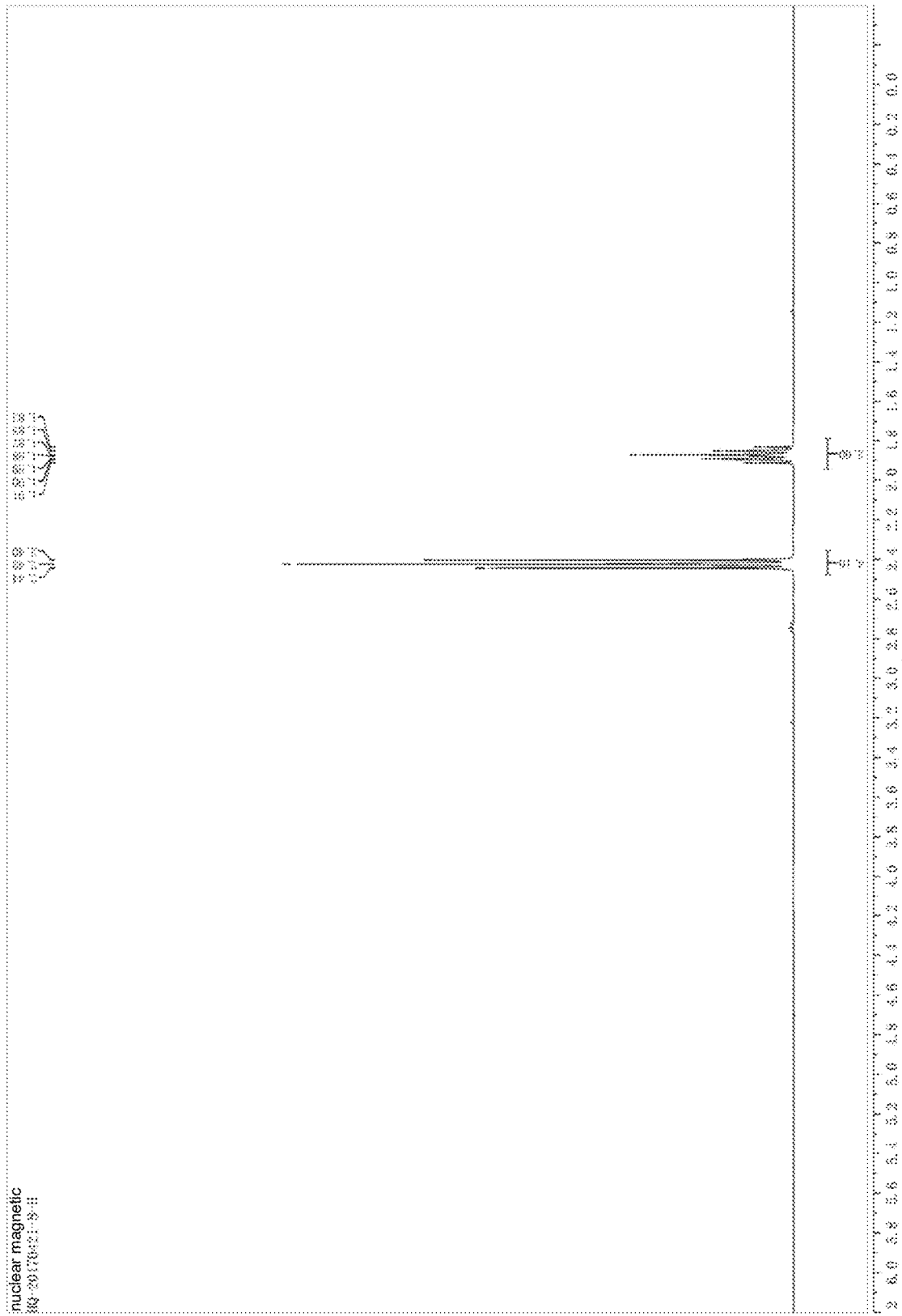
FIG. 10 shows the representative $^1$H-NMR of the 1,1-cyclobutane dicarboxylic acid recovered from alcohol washing in Example 2.

The filtrate was rotary evaporated to dryness under vacuum, 20.5 g of of residue remained, NMR (see also FIG. 10) ($D_2O$) δ; 1.87, pent, 2H; 2.42, t, 4H, shown to be a fairly pure 1,1-cyclobutane dicarboxylic acid, mixed by small amount of alcohol.

Figure 11:
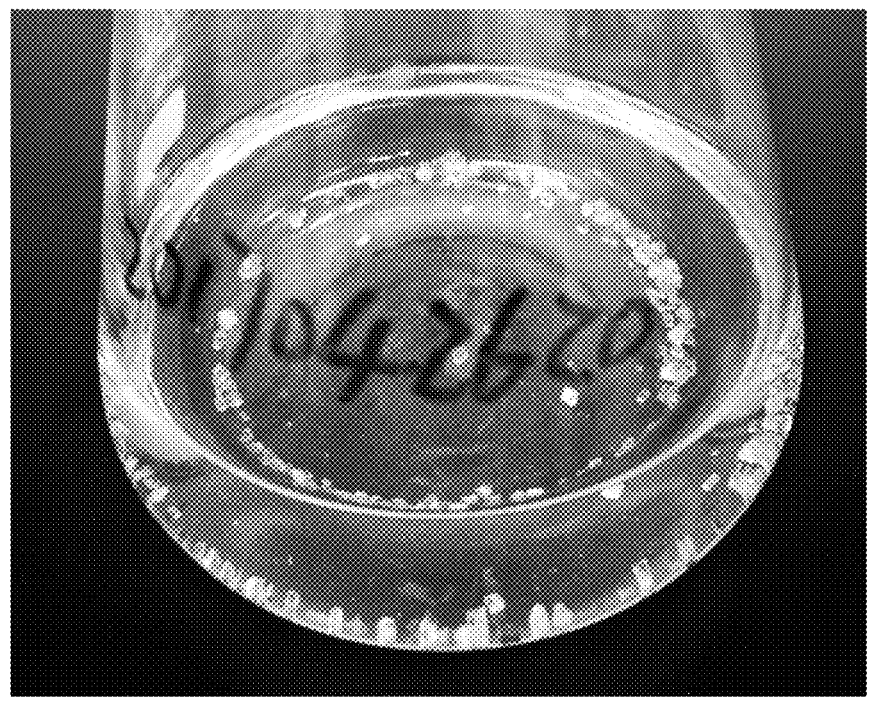
FIG. 11 shows the representative picture of the product crystal of Example 2, which is particle crystal of carboplatin.
Figure 12:
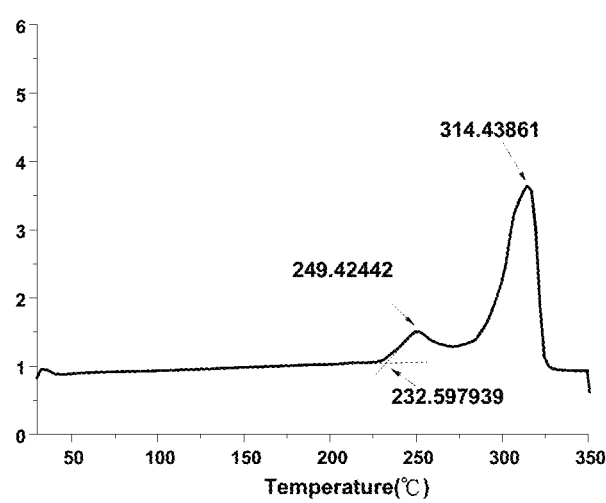
FIG. 12 shows the representative DSC curve of the crystal product of Example 2, which shows melting point of 232.6° C.

Took the above mentioned crude Dicyclpoplatin 3.4 g (total quantity 6.6 g) to continuously simulate the operation "distilled water recrystallization" of Example 1 of inventor's patent CN1311183A; It was dissolved in 100 g of pure water at 42° C., crystallized at 12° C. in refrigerator. Beautiful particle crystals precipitated by 1 day (see also FIG. 11), moved into 4° C. refrigerator, filtered 16 days later. The obtained crystals weighed 1.1 g after vacuum dried, NMR (see also FIG. 9): ($D_2O$) δ, 1.80, pent, 2H; 2.77. t, 4H shown to be carboplatin, Its DSC trace see also FIG. 12, mp 232.6° C. The recovery yield to the amount spent for the reaction was 44.7%.

The following conclusions were drawn from the example:

1, The procedure of the inventor's patent only produced carboplatin, not the desired product Dicycloplatin.

2, Comparing the crystal products before and after alcohol washing, NMR spectra showed that the former was a mixture of Dicycloplatin containing some remnants of dicarboxylic acid at about 3%, while the later contained carboplatin at around 15%. This would suggest that the weightiness of the integral value of carboplatin peak increased. The increased part of carboplatin was coming from the decomposition of Dicycloplatin by alcohol and by the trace amount of water contaminated in the crude Dicycloplatin. So, it could be deduced that alcohol decomposed Dicycloplatin and alcohol washing was not a safe procedure to purify Dicycloplatin. The original inventor's process of washing with alcohol was not appropriate.

Figure 13:
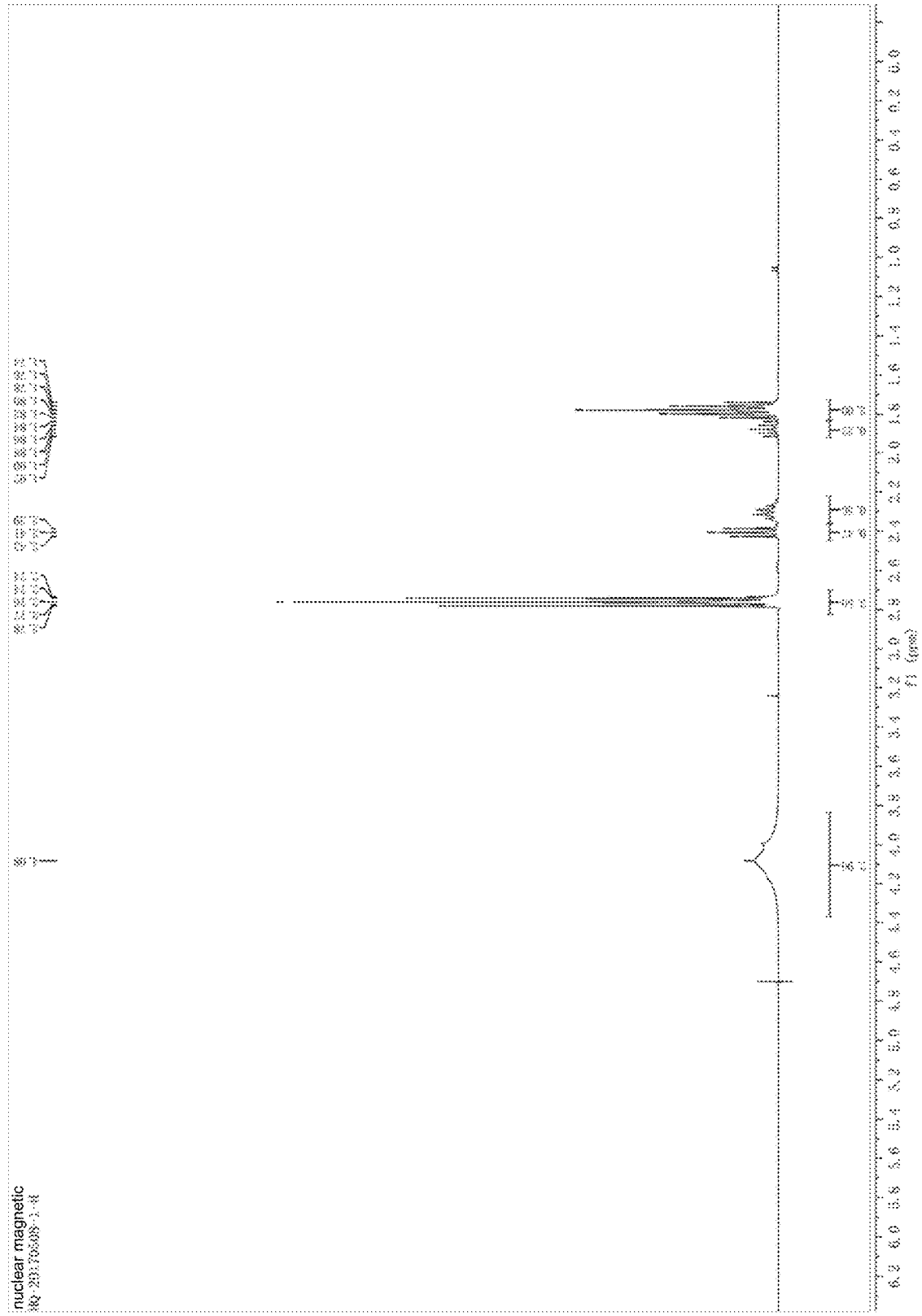
FIG. 13 shows the representative $^1$H-NMR of the product of Example 2, which experienced alcohol washing and then isopropanol treatment. Its major part was carboplatin, while containing Dicycloplatin at around 12%.

In order to further study the decomposition of Dicycloplatin by alcohol, we conducted the following experiments:

Isopropanol 5.0 ml was added to 115.6 mg of the dry product after alcohol washing, stirred at room temperature overnight, filtered, 85 mg of cake was obtained, NMR (see also FIG. 13): ($D_2O$) δ, 1.78, pent, 2H (2.00, the part of carboplatin); 1.88, pent, 2H, (0.22, the part of dicarboxylic acid); 2.41, t, 4H (the part of dicaroxylic acid); 2.76, t, 4H (the part of carboplatin). This suggested that the sample was carboplatin mixed by Dicycloplatin at around 12%.

Figure 14:
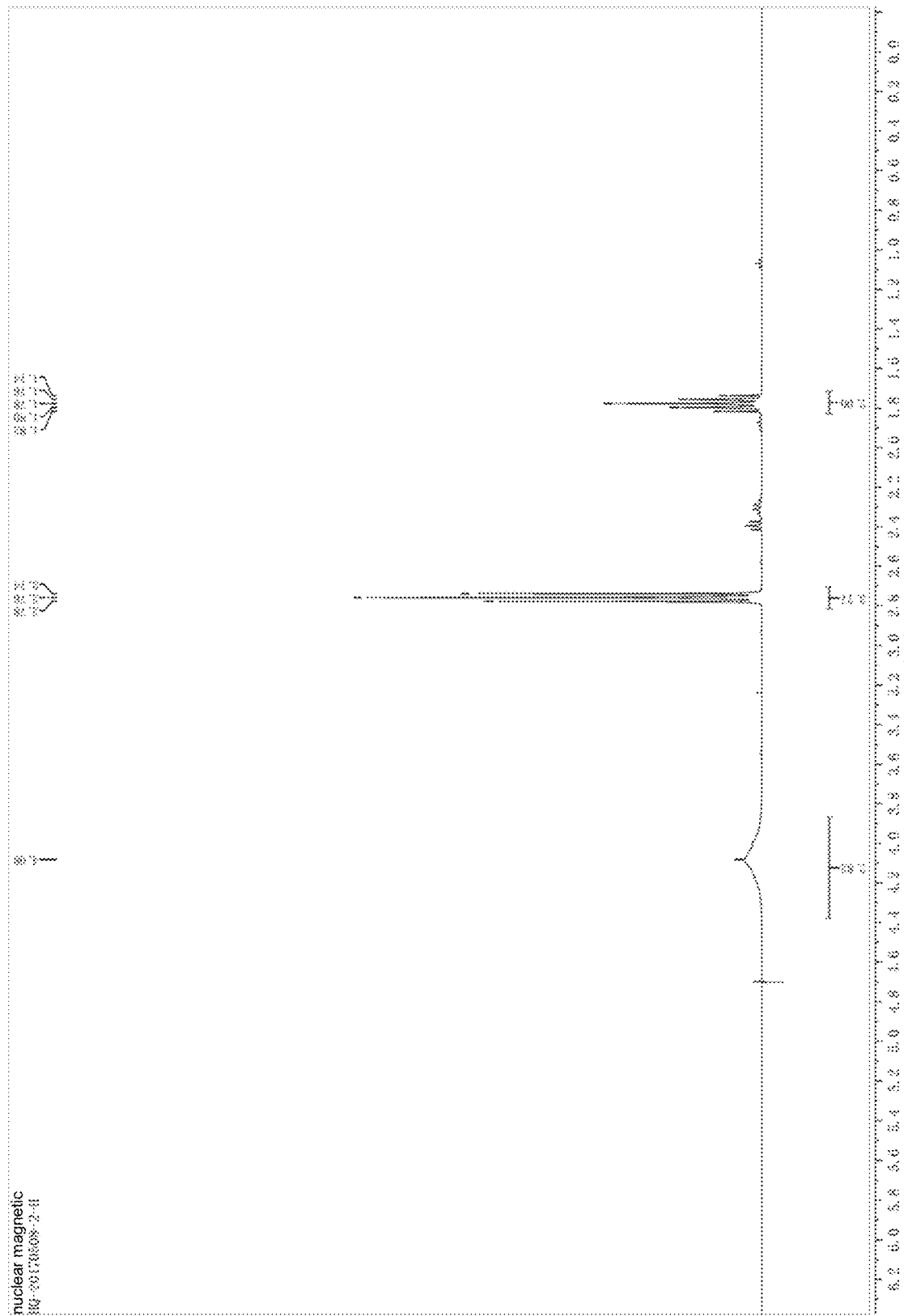
FIG. 14 shows the representative $^1$H-NMR of the product of Example 2, which experienced alcohol washing and then alcohol treatment. Its major part was carboplatin, while containing Dicycloplatin at less than 2%. This means that alcohol has a stronger ability to decompose Dicycloplatin than isopropanol.

5.0 ml of ethyl alcohol was added to 119.3 mg of the dry product after alcohol washing, stirred at room temperature overnight, filtered, 78 mg of cake was obtained, NMR (see also FIG. 14): ($D_2O$) δ, 1.78, pent, 2H (2.00, the part of carboplatin); 1.88, pent, 2H, (<0.05, the part of dicarboxylic acid); 2.41, t, 4H (the part of dicaroxylic acid); 2.76, t, 4H (the part of carboplatin). This suggested that the sample was carboplatin mixed by Dicycloplatin at less than 2%.

Compare the above two products with each other, the majority content of both products were carboplatin, with the former containing more Dicycloplatin (12%) than the later (2%). That would suggest that under the same conditions, the decomposition effect of Dicycloplatin by isopropanol was significantly less pronounced than the effect by ethanol.

If we compare the above two products with the products before alcohol treatment, one more conclusion could be drawn that Dicycloplatin, when co-existing with dicarboxylic acid, showed stronger resistance to alcohol than Dicycloplatin alone.

3, The decomposition effect of water was much stronger than alcohol. Dicycloplatin decomposed in water completely and thoroughly. So that "recrystallization of Dicycloplatin with distilled water" could only yield carboplatin. Example 1 of the original inventor's patent used water to recrystallize after the product was first washed with alcohol. Thus, the product came out must be the starting carboplatin.

Example 3, the Example Simulated Example 1 of Patent CN104693245A

Figure 15:
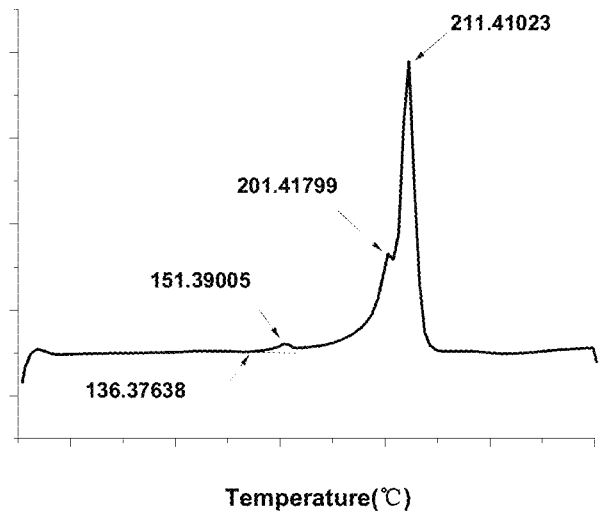
FIG. 15 shows the representative DSC curve of the product of Example 3.

Carboplatin 5.1 g (137.4 mmol) and dicarboxylic acid 2.0 g (138.8 mmol, $MR_{DA/KB}$=1.0) were added to 225 ml of pure water, stirred at room temperature (25° C.) for 2.5 hours to dissolve. The stirring was continued for 1 more hour, standed at room temperature for 7 days under the condition of avoiding light. Then it was rotary evaporated to driness at 40° C. to furnish a residue 7.05 g, yield 99.3%. It was a crystalline powder by naked eye observation, and a mixture of fine needles and very finely broken particles under microscope (two crystal appearances meant to be a mixture). Mp 165.3° C. turned gray in color, 185.2° C. black speck appeared, 200.2° C. turned all dark. DSC (see also FIG. 15) showed the peak of dicarboxylic acid at the beginning, then raised up gradually to the peak of Dicycloplatin. The trace showed the characteristic of carboplatin. It was obviously a mixture.

Example 4, the Example Simulated Strictly Example 5 of Patent CN106132408A, Only the Preparation Scale was Reduced Dicarboxylic acid 2.53 g (175.5 mmol) was added into 25 ml of pure water, stirred at room temperature under the condition of avoiding light. The acid fully dissolved immediately. Carboplatin 5.0 g (134.7 mmol, $MR_{DA/KB}$ equaled to 1.30) was added into the solution. A milky white suspension was formed with stirring. The reaction mixture was further stirred for 6 hours. Pieces of ice were added into the bath in batches, with the cooling rate controlled at 20° C. per hour, the reaction mixture was cooled down to 5° C. It was then moved into 5° C. refrigerator to crystallize for 19 hours. Throughout the entire process, the reaction mixture was heterogeneous. It was then filtered, the filter cake was washed with tiny amount of water, dried under vacuum, a solid of 6.2 g resulted, yield 89.3%, mp 202.4° C. turned gray, 205.2° C. tarred.

Figure 16:
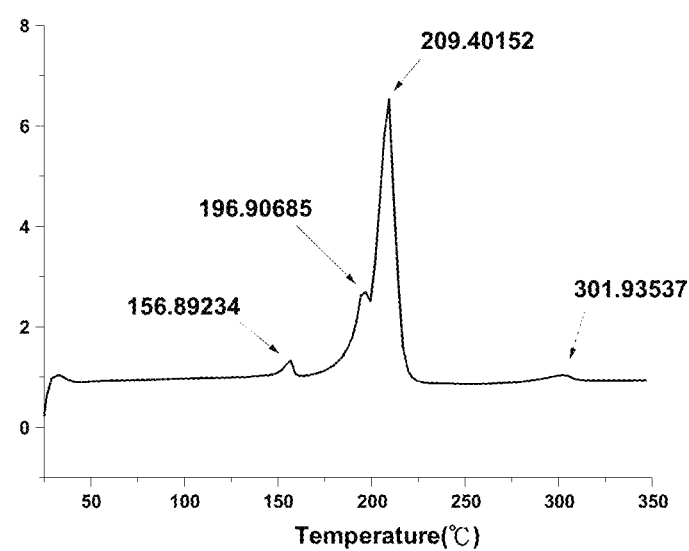
FIG. 16 shows the representative DSC curve of the product of Example 5.

Example 5, the Example Strictly Simulated the Example 7 of Patent CN106132408A, Only Scaled Up by 10 Times Carboplatin 500 mg (1.347 mmol) was added into 28 ml of water, 40 min later, dicarboxylic acid 194 mg (1.346 mmol, $MR_{DA/KB}$ equaled to 1 to 1) was added, a clear solution formed quickly. The stirring was continued for 70 min. The reaction solution was rotary evaporated to driness at 50-55° C. under vacuum to result in 689 mg of white powder, yield 99.3%. The product was still powdery under microscope, mp 183.0° C. turned gray, 193.4° C. turned dark, 202.7° C. turned all black under microscope. The long range of melting point suggested a mixture. For its DSC trace, please see also FIG. 16.

Example 6, at the Ratio $MR_{DA/KB}$ of Equaled to 5.2, Utilized the Preparation Mother Liquor by 3 Additional Cycles. At Every Cycle, Both of the Starting Materials Carboplatin and Dicarboxylic Acid were Supplemented in the Amounts Calculated on the Basis of the Amount of Dicycloplatin Obtained in Previous Run The first run of the preparation: Carboplatin 10 g (26.9 mmol) and 1,1-cyclobutane dicarboxylic acid 20.1 g (139.5 mmol, $MR_{DA/KB}$ equaled to 5.2) were dissolved in 400 ml of pure water ($H_2O/KB$ equaled to 40) at 35° C., stirred up to fully dissolve at the temperature around half an hour. The stirring was continued for more 30 min, 2.0 g of active charcoal was added, stirred at the temperature for 30 min, filtered, the filter cake was washed with pure water 2×4 ml (2% of the amount for the preparation), the washing was combined with the filtrate. The obtained solution was transferred into a crystallization flask, natural cooling down to room temperature, then stored in a refrigerator of 12° C. for 5 days, moved to refrigerator of 4° C. to crystallize. Needle crystals appeared, grew in size, and increasing in greater quantity in a few days, formed transparent crusters like pieces of flower. The process lasted over half a month; filtered, dried in vacuum. The product of the first run of the preparation weighed 8.15 g, yield 58.7%.

The second run of the preparation: The filtrate resulted from the first run weighed 423.0 g, the loss during that run was neglected, according to the amount of the first run product (8.15 g), the reduced reactants in the system were: carboplatin 5.87 g and dicarboxylic acid 2.28 g. Supplemented the amounts of the reactants, run the reaction at 35° C. for 30-60 min. 2.0 g of active charcoal was added, stirred at the same temperature for 30 min, filtered, the filter cake was washed with pure water 2×4 ml, the washing was combined with the filtrate. The obtained solution was transferred into a crystallization flask, natural cooled down to room temperature, then stored in a refrigerator of 12° C. for 5 days, moved to refrigerator of 4° C. to crystallize; filtered, sprayed with pre-cooled 5° C. isopropanol and ethyl acetate successively, dried at room temperature in vacuum, 8.00 g of the desired product was obtained. 5.87 g of carboplatin was supplemented for this run, yielding 98.2%; 15.87 g of total amount of carboplatin was used in the series of the preparation, resulting in 16.15 g of total amount of the product, yielding 68.9%.

The third run of the preparation: The mother liquor of the second run weighed 432.9 g, neglecting the loss during the process of the second run. Based on the amount of the second run product (8.00 g), the reduced reactants in the system were: carboplatin 5.76 g and dicarboxylic acid 2.24 g. Supplementing the reactants of these amounts, the third run of the preparation was initiated. By the same process, product Dicycloplatin of the third run was obtained in 7.00 g. 5.76 g of carboplatin was supplemented for this run, yielding 87.5%. 21.63 g of the total amount of carboplatin was used in the series of the preparation so far, resulting in 23.15 g of the total amount of the product, yielding 77.10%.

The forth run of the preparation: The amount of the third run produced mother liquor of 413.4 g. Neglecting the loss during the process of the third run, and based on the 7.00 g of the amount of the third run product, the reduced reactants in the system were: carboplatin 5.04 g and dicarboxylic acid 1.96 g. Supplemented the reactants of these amounts, the forth run of preparation was imitated. By the same process, the product Dicycloplatin of the forth run weighed 6.90 g, 5.04 g was the amount of carboplatin supplemented for this run, yield 98.6%; 26.67 g of the total amount of carboplatin was used in the series of the preparation so far, resulting in 30.05 g of the total amount of the product, yielding 81.2%.

The designs and executions of Run 2, 3, and 4 were based on the mother liquor utilization from the previous run and resulted in increases of the overall yield. The products of run 2, 3, and 4 were all good in quality; their melting points showed by DSC curves agreed with the standard sample. On the other hand, the more times the mother liquor was recycled, the less marginal gain we would get on the overall yield. Preferably, the number of recycles should be no more than 5. After the recycle utilization was terminated, the mother liquor would be used for recovery of Dicycloplatin, dicarboxylic acid, and carboplatin.

Because the molar ratio of dicarboxylic acid to carboplatin for the preparation of needle-like Dicycloplatin was stipulated to be higher than 4, using a ratio of 5, the concentration of dicarboxylic acid in the mother liquor was over 3.1%. Using a ratio of 7, the concentration would be over 4.6%. So, it was clear that the obtained product must be contaminated by the mother liquor, namely by dicarboxylic acid that should have been cleaned up. However, because Dicycloplatin decomposed quickly once touched water or alcohol, removing the adsorbed mother liquor became difficult. Our initial solution was to transfer the product onto a piece of filter paper, and then using another piece of paper to absorb the mother liquor on the product. After comparing several different organic solvents, we chose pre-cooled isopropanol to spray the product to first replace the mother liquor, and then using pre-cooled ethyl acetate to clear up the isopropanol. The products through either one of the above procedures qualified the standard of quality on crystal appearance, melting point, and HPLC contents. Because isopropanol also may decompose Dicycloplatin, the spray solvent must be pre-cooled and controlled in quantity, the filter cake spray terminated once the filtrate drops appeared.

Example 7, at the Ratio $MR_{DA/KB}$ of Equaled to 5.15, Utilized the Preparation Mother Liquor for 3 Cycles. At Every Cycle, Both of the Starting Materials Carboplatin and Dicarboxylic Acid were Supplemented in the Amounts Calculated on the Basis of the Amount of Dicycloplatin Obtained in Previous Run The first run of the preparation: Carboplatin 25.0 g (67.33 mmol) and 1,1-cyclobutane dicarboxylic acid 50.0 g (346.98 mmol, $MR_{DA/KB}$ equaled to 5.15) were dissolved in 1125 ml of pure water ($H_2O/KB$ equaled to 45) at 35° C., stirred up to fully dissolve at the temperature in about half an hour. The stirring was continued for an additional 15 to 30 min, 4.2 g of active charcoal was then added, stirred at the temperature for 30 min, filtered, the filter cake was washed with pure water 2×11.25 ml (2% of the amount used for the preparation), the washing was combined with the filtration. The obtained solution was transferred into a crystallization flask, cooled at 8° C. for 2 days. Clusters of crystals appeared, grew large and increased in quantity during the period of time, then was moved into a refrigerator of 4° C. for 15 days, transparent clusters of crystals, like pieces of flower, formed. The product was collected through filtration, sprayed with pre-cooled to 5° C. isopropanol and ethyl acetate successively, dried at room temperature in vacuum, 18.09 g of the product from the first run of preparation was obtained, yielding 52.1%.

The second run of the preparation: The filtrate resulted from the first run weighed 1170.9 g. Loss during that run was neglected, based on the amount of the first run product (18.09 g), the reduced reactants in the system were: carboplatin 13.03 g and dicarboxylic acid 5.06 g. supplemented the amounts of the reactants, run the reaction at 35° C. for 30-60 min. 5.0 g of active charcoal was added, stirred at the same temperature for 30 min, filtered, the filter cake was washed with pure water 2×11.25 ml, the washing was combined with the filtrate. The obtained solution was transferred into a crystallization flask, natural cooling down to room temperature, then stored in a refrigerator of 12° C. for 3 days, moved to refrigerator of 4° C. for 25 days to crystallize; The same procedure furnished the product of second run of the preparation, weighed 17.00 g. 13.03 g was the amount of carboplatin supplemented for this run, yielding 94.0%. 38.03 g was the total amount of carboplatin used in the series of the preparation so far, resulting in a total amount of the product of 35.09 g, with overall yield reaching 66.5%.

The third run of the preparation: The mother liquor of the second run weighed 1169.9 g. Neglected the loss during the process of the second run, based on the amount of the second run product (17.00 g), the reduced reactants in the system were: carboplatin 12.25 g and dicarboxylic acid 4.75 g. supplemented the reactants of these amounts, stirred at 35° C. for 30-60 min, 5.0 g of active charcoal was added, stirred at the same temperature for 30 min, filtered, the filter cake was washed with pure water 2×11.25 ml. The washing was combined with filtrate. The solution obtained was transferred into a crystallization flask, natural cooling down to rt, moved into a 12° C. refrigerator for 3 days, transferred into 4° C. refrigerator for 25 days under the condition of avoiding light. The product of the third run was collected. It weighed 15.90 g. 12.25 g was the amount of carboplatin supplemented for this run, yielding 93.5%. 50.28 g was the total amount of carboplatin used in the series of the preparation so far, resulting in 50.99 g of the total amount of the product, with 73.1% of the overall yield.

The forth run of the preparation: The amount of the third run gave mother liquor 1167.8 g, neglected the loss during the process of third run, based on the amount of the third run product (15.90 g), the reduced reactants in the system were: carboplatin 11.46 g and dicarboxylic acid 4.44 g. supplemented the reactants of these amounts, stirred for 30-60 min at 35° C. 5 g of active charcoal was added to de-colorize, stirred for 30 min at the same temperature. filtered, the filter cake was washed with pure water 2×11.25 ml. The washing was combined with filtrate. The solution obtained was transferred into a crystallization flask, natural cooling down to rt, moved into a 12° C. refrigerator for 3 days, transferred into 4° C. refrigerator for 25 days under the condition of avoiding light. The product of the forth run was collected. It weighed 16.95 g. 11.46 g was the amount of carboplatin supplemented for this run, yielding 106.6%; 61.71 g was the total amount of carboplatin used in the series of the preparation so far, resulting in 67.95 g of the total amount of the product, with overall yield reaching 79.3%.

Example 8: at the Ratio $MR_{DA/KB}$ of Equaled to 4.5, Utilized the Preparation Mother Liquor by 3 Cycles. At Every Cycle, Both of the Starting Materials Carboplatin and Dicarboxylic Acid were Supplemented in the Amounts Calculated on the Basis of the Amount of Dicycloplatin Obtained in Previous Run The first run of the preparation: Carboplatin 50.1 g (134.9 mmol) and 1,1-cyclobutane dicarboxylic acid 87.5 g (607.2 mmol, $MR_{DA/KB}$ equaled to 4.5) were dissolved in 2250 ml of pure water ($H_2O$/KB equaled to 45) at 35° C., stirred up to fully dissolve at the temperature in about half an hour. The stirring was continued for an additional 15 to 30 min, 10 g of active charcoal was added, stirred at the temperature for 30 min, filtered, the filter cake was washed with pure water 2×22.5 ml (2% of the amount used for the preparation), the washing was combined with the filtrate. The obtained solution was transferred into a crystallization flask, cooled at 8° C. for 2 days, During the period of time, cruster of crystals appeared and grew large, increased in quantity. Then it was moved into a refrigerator of 4° C. for 15 days, transparent crusters of crystals like flower was obtained. The product was collected through filtration, sprayed with pre-cooled to 5° C. of isopropanol and of ethyl acetate successively, dried at room temperature in vacuo, 36.8 g of product from the first run of preparation was obtained, yield 52.9%.

The second run of the preparation: The filtrate resulted from the first run weighed 2307.1 g, the loss during that run was neglected, calculated on the basis of the amount of first run product (36.8 g), the reduced reactants in the system were: carboplatin 26.5 g and dicarboxylic acid 10.3 g. supplemented the amounts of the reactants, run the reaction at 35° C. for 30-60 min. 10 g of active charcoal was added, stirred at the same temperature for 30 min, filtered, the filter cake was washed with pure water 2×22.5 ml, the washing was combined with the filtrate. The obtained solution was transferred into a crystallization flask, natural cooling down to room temperature, then stored in a refrigerator of 12° C. for 3 days, moved to refrigerator of 4° C. for 25 days to crystallize; The same procedure furnished the product of second run of the preparation, weighed 32.3 g. 26.5 g was the amount of carboplatin supplemented for this run, yielding 87.8%. 76.6 g was the total amount of carboplatin used in the series of preparation so far, resulting in a total amount of the product of 69.1 g, with overall yield 65.0%.

The third run of the preparation: The mother liquor of the second run weighed 2270.7 g, neglected the loss during the process of the second run, calculated on the basis of the amount of the second run product (32.3 g), the reduced reactants in the system were: carboplatin 23.3 g and dicarboxylic acid 9.0 g. supplemented the reactants of these amounts, stirred at 35° C. for 30-60 min, 10 g of active charcoal was added, stirred at the same temperature for 30 min, filtered, the filter cake was washed with pure water 2×22.5 ml. The washing was combined with filtrate. The solution obtained was transferred into a crystallization flask, natural cooling down to room temperature, moved into a refrigerator of 12° C. for 3 days, transferred into a refrigerator of 4° C. for 25 days under the condition of avoiding light. The product of the third run was collected in 37.6 g. 23.3 g was the amount of carboplatin supplemented for this run, yielding 116.3%. 99.9 g was the total amount of carboplatin used in the series of preparation so far, resulting in a total amount of the product of 106.7 g, with overall yield 76.9%.

The forth run of the preparation: The amount of the third run gave mother liquor 2300 g, neglected the loss during the process of third run, based on the amount of the third run product (37.6 g), the reduced reactants in the system were: carboplatin 27.1 g and dicarboxylic acid 10.5 g. supplemented the reactants of these amounts, stirred for 30-60 min at 35° C. 10 g of active charcoal was added to de-colorize, stirred for 30 min at the same temperature filtered, the filter cake was washed with pure water 2×22.5 ml. The washing was combined with filtrate. The solution obtained was transferred into a crystallization flask, natural cooling down to room temperature, moved into a refrigerator of 12° C. for 3 days, transferred into a refrigerator of 4° C. for 25 days under the condition of avoiding light. The product of the forth run was collected, weighed 35.8 g. 27.1 g was the amount of carboplatin supplemented for this run, yielding 95.2%. 127.0 g was the total amount of carboplatin used in the series of preparation so far, resulting in a total amount of the product of 142.5 g, with overall yield 80.8%.

Example 9: Experiment at the Scale of 150 g Carboplatin the First Run of the Preparation: At the Ratio $MR_{DA/KB}$ of 6.0, Utilized the Preparation Mother Liquor by 4 Cycles. At Every Cycle, Both of the Starting Materials Carboplatin and Dicarboxylic Acid were Supplemented in the Amounts Calculated on the Basis of the Amount of Dicycloplatin Obtained in Previous Run Carboplatin 150.0 g (0.404 mol) and 1,1-cyclobutane dicarboxylic acid 349.0 g (2.424 mol, $MR_{DA/KB}$ equaled to 6) were dissolved in 6.75 L of pure water ($H_2O$/KB equaled to 45) at 42° C., stirred up to fully dissolve at the temperature. The stirring was continued for additional 15 to 30 min, 30.0 g of active charcoal was added, stirred at the temperature for 30 min, filtered, the filter cake was washed with pure water 2×65 ml, the washing was combined with the filtrate. The obtained solution was transferred into a crystallization flask, cooled at 12° C. for 3 days, During the period of time, cruster of crystals appeared and grew large and increased in quantity, then was moved into a refrigerator of 4° C. for 15 days, transparent crusters of crystals like flower was obtained. The product was collected through filtration, sprayed with pre-cooled to 5° C. of isopropanol and of ethyl acetate successively, dried at room temperature in vacuo, the product of first run of the preparation weighed 131.4 g, yield 63.1%.

The second run of the preparation: The filtrate resulted from the first run weighed 7225.3 g, the loss during that run was neglected, calculated on the basis of the amount of the first run product (131.4 g), the reduced reactants in the system were: carboplatin 94.7 g and dicarboxylic acid 36.7 g. supplemented the amounts of the reactants, run the reaction at 42° C. for 30-60 min. 30.0 g of active charcoal was added, stirred at the same temperature for 30 min, filtered, the filter cake was washed with pure water 2×65 ml, the washing was combined with the filtrate. The obtained solution was transferred into a crystallization flask, natural cooling down to room temperature, then stored in a refrigerator of 12° C. for 3 days, moved to refrigerator of 4° C. for 25 days to crystallize under the condition of avoiding light; The same procedure furnished the product of second run of the preparation, weighed 129.7 g. 94.7 g was the amount of carboplatin supplemented for this run, yielding 98.7%. 244.7 g was the total amount of carboplatin used in the series of preparation so far, resulting in a total amount of the product of 261.1 g, with overall yield 76.9%.

The third run of the preparation: The mother liquor of the second run weighed 7243.8 g, neglected the loss during the process of the second run, calculated on the basis of the amount of the second run product (129.7 g), the reduced reactants in the system were: carboplatin 93.4 g and dicarboxylic acid 36.3 g. supplemented the reactants of these amounts, stirred at 42° C. for 30-60 min, 30.0 g of active charcoal was added, stirred at the same temperature for 30 min, filtered, the filter cake was washed with pure water 2×65 ml. The washing was combined with filtrate. The solution obtained was transferred into a crystallization flask, natural cooling down to rt, moved into a refrigerator of 12° C. for 3 days, transferred into a refrigerator of 4° C. for 25 days under the condition of avoiding light. The product of the third run was collected in 128.5 g. 93.4 g was the amount of carboplatin supplemented for this run, yielding 99.1%. 338.1 g was the total amount of carboplatin used in the series of preparation so far, resulting in a total amount of the product of 389.6 g, with overall yield 83.0%.

The forth run of the preparation: The amount of the third run gave mother liquor 7256.1 g, neglected the loss during the process of third run, calculated on the basis of the amount of the third run product (128.5 g), the reduced reactants in the system were: carboplatin 92.6 g and dicarboxylic acid 35.9 g. supplemented the reactants of these amounts, stirred for 30-60 min at 42° C. 30.0 g of active charcoal was added to de-colorize, stirred for 30 min at the same temperature. filtered, the filter cake was washed with pure water 2×65 ml. The washing was combined with filtrate. The solution obtained was transferred into a crystallization flask, natural cooling down to room temperature, moved into a refrigerator of 12° C. for 3 days under the condition of avoiding light, transferred into a refrigerator of 4° C. for 25 days. The product of the forth run was collected, weighed 127.7 g. 92.6 g was the amount of carboplatin supplemented for this run, yielding 99.4%. 430.7 g was the total amount of carboplatin used in the series of preparation so far, resulting in a total amount of the product of 517.3 g, with overall yield 83.0%.

The fifth run of the preparation: The amount of the forth run gave mother liquor 7263.2 g, neglected the loss during the process of forth run, calculated on the basis of the amount of the forth run product (127.7 g), the reduced reactants in the system were: carboplatin 92.0 g and dicarboxylic acid 35.7 g. supplemented the reactants of these amounts, stirred for 30-60 min at 42° C. 30.0 g of active charcoal was added to de-colorize, stirred for 30 min at the same temperature; filtered, the filter cake was washed with pure water 2×65 ml. The washing was combined with filtrate. The solution obtained was transferred into a crystallization flask, natural cooling down to room temperature, moved into a refrigerator of 12° C. for 3 days under the condition of avoiding light, transferred into a refrigerator of 4° C. for 25 days. The product of the fifth run was collected. It weighed 123.5 g. 92.0 g was the amount of carboplatin supplemented for this run, yielding 96.7%. 522.7 g was the total amount of carboplatin used in the series of preparation so far, resulting in a total amount of the product of 640.8 g, with overall yield 83.3%. The fifth run resulted its mother liquor 7277.1 g.

Example 10, at the Ratio of $MR_{DA/KB}$=7.0, Utilized the Preparation Mother Liquor by 5 Cycles. At Every Cycle, Both of the Starting Materials Carboplatin and Dicarboxylic Acid were Supplemented in the Amounts of Materials Remained in Mother Liquor after the Previous Run that were Detected by HPLC The first run of the preparation: Carboplatin 10.0 g (0.027 mol) and 1,1-cyclobutane dicarboxylic acid 27.2 g (0.189 mol, $MR_{DA/KB}$ equaled to 7) were dissolved in 450 ml of pure water ($H_2O/KB$ equaled to 45) at 42° C., stirred up to fully dissolve at the temperature. The stirring was continued for additional 15 to 30 min, 2.0 g of active charcoal was added, stirred at the temperature for 30 min, filtered, the filter cake was washed with pure water 10 ml, the washing was combined with the filtrate. The obtained solution was transferred into a crystallization flask, cooled at 12° C. for 11 days, During the period of time, cruster of crystals appeared and grew large. It was moved into a refrigerator of 4° C. for 7 days, transparent crusters of crystals like flower were obtained. The product was collected through filtration, sprayed with pre-cooled to 5° C. of isopropanol and of ethyl acetate successively, dried at room temperature in vacuum, the product of first run of preparation was obtained in 8.963 g, yield 64.6%.

The mother liquor collected measured 474 ml, HPLC analysis: carboplatin, 4.9382 mg/ml, dicarboxylic acid, 48.0559 mg/ml.

The second run of the preparation: based on the HPLC analysis, first run mother liquor contained carboplatin 2.3407 g and dicarboxylic acid 22.7789 g. Supplemented the starting materials in the amounts equaled to the reduced amount due to the previous reaction, namely carboplatin 7.6593 g and dicarboxylic acid 4.4215 g. The reaction was run at 42° C. for 30 min, added 2.0 g of active charcoal, stirred at the same temperature for 30 min. filtered, the filter cake was washed with pure water 10 ml. The washing was combined with filtrate. The solution obtained was transferred into a crystallization flask, natural cooling down to room temperature, moved into a refrigerator of 12° C. for 8 days under the condition of avoiding light, transferred into a refrigerator of 4° C. for 12 days. The product of the second run was collected. It weighed 9.9907 g. 7.6593 g was the amount of carboplatin supplemented for this run, yielding 94.0%. 17.6593 g was the total amount of carboplatin used in the series of preparation so far, resulting in a total amount of the product of 18.9537 g, with overall yield 77.3%.

The mother liquor collected measured 470 ml, 5 ml of pure water was supplemented. HPLC analysis: carboplatin, 4.8322 mg/ml, dicarboxylic acid, 49.1537 mg/ml.

The third run of the preparation: based on the HPLC analysis, second run mother liquor contained carboplatin 2.2953 g and dicarboxylic acid 23.348 g. Supplemented the starting materials in the amounts equaled to the reduced amount due to the previous run, namely carboplatin 7.7047 g and dicarboxylic acid 3.852 g. The reaction was run at 42° C. for 30 min, added 2.0 g of active charcoal, stirred at the same temperature for 30 min. filtered and washed. The solution obtained was transferred into a crystallization flask, natural cooling down to rt, moved into a refrigerator of 12° C. for 8 days under the condition of avoiding light, transferred into a refrigerator of 4° C. for 14 days. The product of the third run was collected. It weighed 9.8238 g. 7.7047 g was the amount of carboplatin supplemented for this run, yielding 91.9%. 25.364 g was the total amount of carboplatin used in the series of preparation so far, resulting in a total amount of the product of 28.7775 g, with overall yield 81.7%.

The mother liquor collected in 450 ml, HPLC analysis: carboplatin, 5.2417 mg/ml, dicarboxylic acid, 47.6019 mg/ml.

The fourth run of the preparation: based on the HPLC analysis, third run mother liquor contained carboplatin 2.3588 g and dicarboxylic acid 21.4209 g. Supplemented water 25 ml, carboplatin 7.6412 g and dicarboxylic acid 5.7791 g. The reaction was run at 42° C. for 30 min, added 2.0 g of active charcoal, stirred at the same temperature for 30 min. filtered; the filter cake was washed with 15 ml of water. The solution obtained was transferred into a crystallization flask, natural cooling down to room temperature, moved into a refrigerator of 12° C. for 8 days under the condition of avoiding light, transferred into a refrigerator of 4° C. for 14 days. The product of the fourth run was collected. It weighed 9.9577 g. 7.6412 g was the amount of carboplatin supplemented for this run, yielding 93.9%. 33.0052 g was the total amount of carboplatin used in the series of preparation so far, resulting in a total amount of the product of 38.7352 g, with overall yield 84.5%.

The mother liquor collected in 485 ml, HPLC analysis: carboplatin, 4.7729 mg/ml, dicarboxylic acid, 48.9198 mg/ml.

The fifth run of the preparation: based on the HPLC analysis, the forth run mother liquor contained carboplatin 2.3149 g and dicarboxylic acid 23.7261 g. Supplemented the starting materials in the amounts equaled to the reduced amount due to the previous run, namely carboplatin 7.6851 g and dicarboxylic acid 3.4739 g. The reaction was run at 42° C. for 30 min, added 2.0 g of active charcoal, stirred at the same temperature for 30 min. filtered and washed. The solution obtained was transferred into a crystallization flask, natural cooling down to room temperature, moved into a refrigerator of 12° C. for 8 days under the condition of avoiding light, transferred into a refrigerator of 4° C. for 14 days. The product of the fifth run was collected. It weighed 9.9967 g. 7.6851 g was the amount of carboplatin supplemented for this run, yielding 93.7%. 40.6903 g was the total amount of carboplatin used in the series of preparation so far, resulting in a total amount of the product of 48.7319 g, with overall yield 86.3%.

The mother liquor measured 470 ml, HPLC analysis: carboplatin, 5.0647 mg/ml, dicarboxylic acid, 48.0071 mg/ml.

The sixth run of the preparation: based on the HPLC analysis, the fifth run mother liquor contained carboplatin 2.3084 g and dicarboxylic acid 22.5633 g. Supplemented water 5 ml, carboplatin 7.6196 g and dicarboxylic acid 4.6367 g. The reaction was run at 42° C. for 30 min, added 2.0 g of active charcoal, stirred at the same temperature for 30 min. filtered and washed. The solution obtained was transferred into a crystallization flask, natural cooling down to rt, moved into a 12° C. refrigerator for 8 days under the condition of avoiding light, transferred into 4° C. refrigerator for 12 days. The product of the sixth run was collected. It weighed 9.8984 g. 7.6196 g was the amount of carboplatin supplemented for this run, yielding 93.6%. 48.3099 g was the total amount of carboplatin used in the series of preparation so far, resulting in a total amount of the product of 58.6303 g, with overall yield 87.4%.

Figure 17:
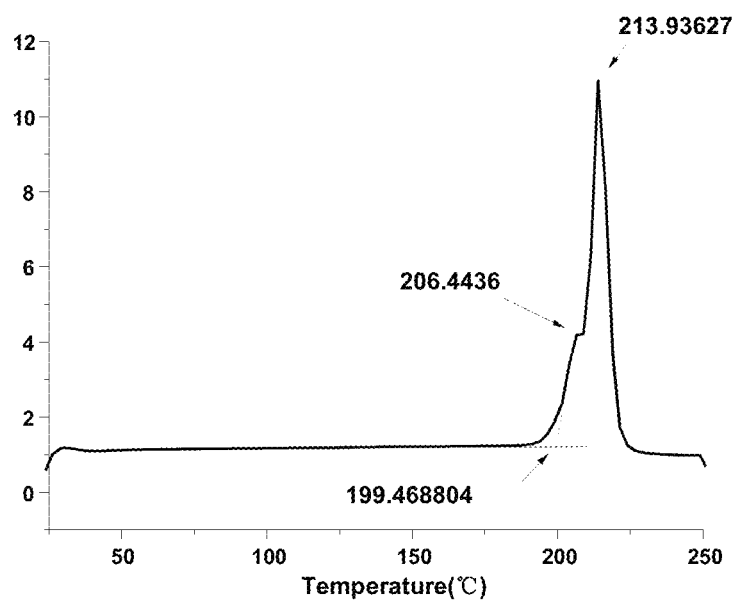
FIG. 17 shows the representative DSC curve of the product of Example 11, which showed melting point of 199.5° C. The $MR_{DA/KB}$ was 7.0 in the preparation.
Figure 18:
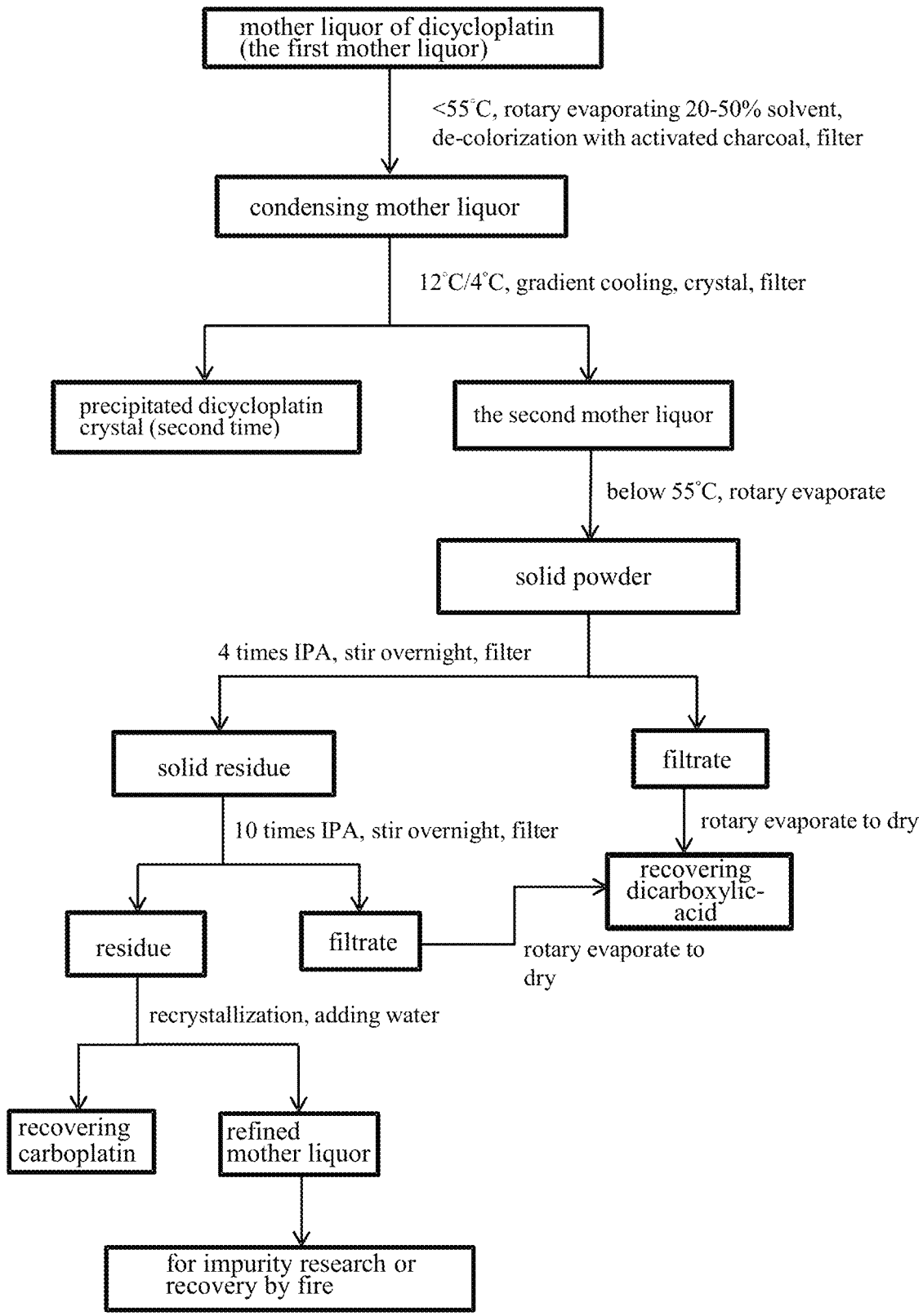
FIG. 18 shows the representative process flow chart of the mother liquor treatment in dicycloplatin production.

Example 11, at the Ratio of $MR_{DA/KB}=7.0$, the Preparation Mother Liquor was Spent on Recovery of the Second Crop of Dicycloplatin, and then the Second Mother Liquor was Used to Recover Carboplatin 1,1-cyclobutane dicarboxylic acid 54.34 g (377.10 mmol) was added into pure water 1000 ml. It was stirred at 42° C. for 30 min to dissolve. Into the solution Carboplatin 20.0 g (53.86 mmol, $MR_{DA/KB}=7.0$) was added, stirred at the same temperature for 20 min. A clear solution was formed. After the stirring was continued for additional 20 min, 3.06 g of active charcoal was added, and continuously stirred for 30 min, filtered. Natural cooling for 4 hrs, moved into a refrigerator of 12° C. for 2 days, needle-like crystals appeared. Then it was moved into a refrigerator of 4° C. for 19 days. The crystals were collected by filtration, natural dried at rt. Colorless needle-like crystals were obtained, 17.95 g, yield 64.64%. Its DSC trace as shown as FIG. 17.

The container was rinsed with small amount of pure water; the filtrate weighed 1063.1 g. Half of it (532 g) was rotary evaporated in parts under vacuum to dryness at 40° C., that resulted residue 28.2 g. The residue was added into the rest half of the filtrate, heated at 40° C. (bath temperature) for 10 min to dissolve. Active charcoal 1.0 g was added to de-colorize for 30 min at the same temperature; filtered; standed at rt for 4 hrs, then moved into a refrigerator of 12° C. Crystal appeared on next day; moved into a refrigerator of 4° C. for 14 days. The colorless needle-like crystals were collected, weighed 4.334 g, yield 15.61%; So far the total yield of the product Dicycloplatin reached 80.25%.

The second mother liquor 554.4 g was rotary evaporated under vacuum to dryness at 40° C., that resulted residue 46.4 g. IPA 226 ml (ratio V/W 4.7) was added to the residue, stirred at room temperature for 5 hrs, filtered. The filtrate was rotary evaporated to dryness; pure white crystalline powder was furnished, weighed 42.3 g. It was the first crop of the recovered 1,1-cyclobutane dicarboxylic acid, with 77.8% of the amount of starting acid, corresponding to 90.8% of the theoretical remain (the amount consumed for Dicycloplatin was deducted). Filter cake 5.0 g was resulted at the same time. IPA 65 ml was added (ratio V/W 13); stirred at room temperature overnight, filtered. The filtrate was rotary evaporated to dry, that resulted 0.734 g of residue, it was the second crop of recovered 1,1-cyclobutane dicarboxylic acid. The amount accounted for 1.58% of the amount of theoretical remains. Its HPLC showed some impurities including carboplatin. The filter cake weighed 3.4 g after vacuum dried, it was the recovered crude carboplatin. The crude was added into 84 ml of pure water, dissolved at 75° C., decolorized with active charcoal 1.24 g for 30 min, filtered, cooled down to crystallize, resulted big shining particle crystals; weighed 1.81 g after dried. The amount accounted for 9.1% of the initial carboplatin input. If the amount consumed on Dicycloplatin (yield 80.25%) was deducted, the recovery yield reached 45.8%. So far, the utilization of starting carboplatin reached 89.35%. The mother liquor of carboplatin recrystallization was rotary evaporated to dryness in vacuo; resulted 1.62 g residue. It was burnt together with the waste active charcoal during the preparation to recover platinum. The utilization of the noble metal reached 98%.

Example 12: Recover Dicycloplatin from the Mother Liquor of the Last Cycle of Preparation The mother liquor of Example 9 was used as the starting material of the example.

For Example 9, 522.7 carboplatin (1.408 mol) and 493.6 g 1,1-cyclobutane dicarboxylic acid (3.425 mol) were spent, Dicycloplatin 640.8 was obtained, the overall yield was 88.3%. The preparation resulted mother liquor 7277.1 g, neglected the loss during the series of cycles of preparation, the mother liquor should contain Dicyclopplatin 88.4 g and dicarboxylic acid 290.8 g.

1500 g of the above mother liquor was taken (20.6% of the total), rotary evaporated under vacuum at 55° C. to dryness, resulted residue 70.4 g. The residue was added into the major of the mother liquor, de-colorized with 20 g active charcoal at 45° C. for 1 hr. filtered while hot, the filter cake was washed with 80 ml of pure water, washing was combined with the filtrate, natural cooling to room temperature, moved into a refrigerator of 12° C. to crystallize under the condition of avoiding light. Needle-like crystals appeared 3 days later; moved into a refrigerator of 12° C. for 20 days. The crystals were collected by filtration. Sprayed with pre-cooled 5° C. of isopropanol and ethyl acetate successively, dried at room temperature in vacuo, resulted 41.5 g of Dicycloplatin, with a recovery of 48.9%. Example 9 has given 640.8 g of the product before, so the total output of the preparation reached 682.3 g, equivalent to the yield of 94.0%. The above procedure resulted second mother liquor 5817 g at the same time.

Example 13: Recovering Carboplatin from Second Mother Liquor

Example 12 resulted second mother liquor 5817 g, neglected the loss during the whole process, it should contain Dicycloplatin 43.3 g and dicarboxylic acid 290.8 g. It was rotary evaporated at 55° C. to dryness under vacuum, thoroughly dried under oil pump vacuum overnight, 309.1 g of residue was resulted. The residue was completely washed with alcohol 300 ml×3, filtration gave 52.3 g of cake. The filtrate was the solution of recovered 1,1-dicarboxylic acid. Evaporation furnished dicarboxylic acid 241 g in good quality, recovery yield 82.9%. The filter cake was added into pure water 1500 g, stirred at room temperature for 2 hrs, resulted a slightly turbid solution, decolorized with 8 g of active charcoal at 45° C. for 1 hr, filtered, the filtrate was natural cooling to room temperature, and then moved into a refrigerator of 12° C. until crystals appeared, then moved into 4° C. ice box for 20 days. Filtration gave particle crystals of carboplatin 17.1 g. accounted for 3.27% of the total amount spent for the preparation. So the utilization of starting carboplatin reached 97.3%.

Example 14: Recrystallization of Dicycloplatin

The poor quality Dicycloplatin from various batches during the past 2 years were combined. They were still needle-like crystals but the appearance was not so nice, or mp in between 192.3° C. to 194.5° C., lower than standard mp of 198° C., in total of 9.8 g. It was used to verify the recrystallization technology.

Recrystallization procedure 1, use recrystallization solution number 1: Dissolved 1,1-cyclobutane dicarboxylic acid 15.1 g (104.8 mmol) and carboplatin 3.53 g (9.51 mmol) in 320 ml of pure water to prepare the number 1 solution for recrystallization, 4.9 g (9.51 mmol) of the poor Dicycloplatin was added into the solution, stirred and dissolved at 40° C. 0.5 g of active charcoal was added to de-colorize for half an hour, filtered. The filter cake was washed with pure water, washing was combined with the filtrate. The obtained solution was natural cooled down to room temperature, moved into a refrigerator of 12° C. for 3 days, transferred to a refrigerator of 4° C. for 30 days. The crystals from filtration was sprayed with 5 ml of pre-cooled to 5° C. isopropanol and 5 ml of ethyl acetate successively, moved into a vacuum desiccator to pump off remained solvent, colorless needle-like product was obtained, 6.13 g, with yield 125.1%. During the process, the molar ratio of 1,1-cyclobutane dicarboxylic acid to the poor Dicycloplatin was 11.0; the molar ratio of carboplatin to the poor Dicycloplatin $MR_{KB/DCP}$ was 1 to 1; the ratio of water to the poor Dicycloplatin was 65.3. The reason why the yield of purification was over 100% was that a part of carboplatin in the recrystallization solution was converted to Dicycloplatin.

The mother liquor resulted from the procedure could be treated as mother liquor treatment mentioned above.

Recrystallization procedure 2, use recrystallization solution number 2: 1,1-Cyclobutane dicarboxylic acid 6.85 g (47.54 mmol) was dissolved in 160 ml of pure water to prepare the number 2 solution for recrystallization, 4.90 g (9.51 mmol) of the poor Dicycloplatin was added into the solution, stirred and dissolved at 40° C. 0.3 g of active charcoal was added to de-colorize for half an hour, filtered. The filter cake was washed with pure water 5 ml, washing was combined with the filtrate. The combined solution was natural cooled down to room temperature, moved into a refrigerator of 12° C. for 3 days, transferred to a refrigerator of 4° C. for 30 days. The crystals from filtration was sprayed with 5 ml of pre-cooled to 5° C. isopropanol and 5 ml of ethyl acetate successively, moved into a vacuum desiccator to pump off remained solvent, colorless needle-like product was obtained in 3.1 g, with yield 63.3%. During the process, the molar ratio of 1,1-cyclobutane dicarboxylic acid to the poor Dicycloplatin $MR_{DA/DCP}$ was 5.0; the ratio of water to the poor Dicycloplatin was 32.7. The mother liquor resulted from the process could be treated as mother liquor treatment mentioned above.

What is claimed is:

1. An industrial method of producing needle-like crystals of dicycloplatin in high purity, characterized in that, including the following procedures:
    (1) dissolving carboplatin and 1,1-cyclobutane-dicarboxylic acid in water to form a clear solution, allowing them to react;
    (2) standing the reacting solution of step (1) to crystalize dicycloplatin; wherein crystallization conditions are controlled to obtain a yield of dicycloplatin no higher than 75% to ensure a purity of not lower than 99.5%.

2. The industrial method of producing needle-like crystals of dicycloplatin in high purity according to claim 1, characterized in that, wherein reaction conditions comprise the following: molar ratio of the 1,1-cyclobutane-dicarboxylic acid to the carboplatin is 4-16, reaction time is 0.5-6 hours, deionized water is used as reaction solvent; reaction temperature is in a range of room temperature to 50° C.; a ratio of the solvent water to the carboplatin is 30-55 in weight to weight; and wherein the crystallization conditions comprise de-colorization with activated charcoal, cooling the reacting solution to room temperature within 2-8 hours after de-colorization, standing the solution in a dark refrigerator at 10-14° C. for 4-10 days, and then standing in a 0-6° C. refrigerator to crystallize for 15-30 days.

3. The industrial method of producing needle-like crystals of dicycloplatin in high purity according to claim 1, characterized in that, wherein reaction conditions comprise the following: molar ratio of the 1,1-cyclobutane-dicarboxylic acid to the carboplatin is 4-10, reaction time is 0.5-2 hours, the water is deionized water, reaction temperature is in a range of room temperature to 45° C., the room temperature is 10-35° C.; and wherein the crystallization conditions comprise de-colorization with activated charcoal, cooling the reacting solution to room temperature within 2-8 hours after de-colorization, standing the solution in a dark ice box at 10-14° C. for 4-10 days, and then standing in a 0-4° C. refrigerator to crystallize for 15-30 days.

4. The industrial method of producing needle-like crystals of dicycloplatin in high purity according to claim 1, characterized in that, further including step (3), comprising recovering a mother liquor from step (2) and recycling it in 2 to 6 additional cycles, to give an overall yield of dicycloplatin of over 80%; combining the mother liquor with the amount of 1,1-cyclobutane-dicarboxylic acid and of carboplatin consumed by the previous reaction; and repeating step (1) and step (2).

5. The industrial method of producing needle-like crystals of dicycloplatin in high purity according to claim 1, characterized in that, further including step (4), comprising spraying a product of the dicycloplatin obtained from step (2) or step (3) with pre-cooled isopropanol at 5° C. and pre-cooled ethyl acetate at 5° C. successively.

6. The industrial method of producing needle-like crystals of dicycloplatin in high purity according to claim 1, characterized in that, further including step (5), comprising concentrating a last mother liquor of step (3) at 55° C. in the dark to recover an additional portion of dicycloplatin product to give a total yield greater than 90%.

7. The industrial method of producing needle-like crystals of dicycloplatin in high purity according to claim 1, characterized in that, further including step (6), comprising concentrating to dryness a final mother liquor obtained from step (5) at 55° C. in the dark; recovering an amount of 1,1-cyclobutane-dicarboxylic acid by washing with ethyl alcohol or isopropanol, crystallizing a filter cake from water to recover carboplatin, so that a utilization of the carboplatin is over 97%.

8. The industrial method of producing needle-like crystals of dicycloplatin in high purity according to claim 1 further comprising purifying the dicycloplatin product with an aqueous solution of the 1,1-cyclobutane-dicarboxylic acid or an aqueous solution of both of the 1,1-cyclobutane-dicarboxylic acid and the carboplatin.

* * * * *